(12) United States Patent
De Barry et al.

(10) Patent No.: US 8,993,781 B2
(45) Date of Patent: *Mar. 31, 2015

(54) FLUORESCENT BORON-SUBSTITUTED DIPYRROMETHENES AND USE THEREOF FOR DIAGNOSIS

(75) Inventors: Jean De Barry, Strasbourg (FR); Corinne Liegeois, Strasbourg (FR); Alexandre Haefele, Ostwald (FR); Thomas Bura, Teting sur Nied (FR); Gilles Ulrich, Souffel Weyersheim (FR); Raymond Ziessel, Souffel Weyersheim (FR)

(73) Assignees: Centre National de la Recherche Scientifique, Paris (FR); Universite de Strasbourg, Strasbourg (FR)

( * ) Notice: Subject to any disclaimer, the term of this patent is extended or adjusted under 35 U.S.C. 154(b) by 31 days.

This patent is subject to a terminal disclaimer.

(21) Appl. No.: 13/141,850

(22) PCT Filed: Dec. 28, 2009

(86) PCT No.: PCT/FR2009/001486
§ 371 (c)(1),
(2), (4) Date: Aug. 2, 2011

(87) PCT Pub. No.: WO2010/076433
PCT Pub. Date: Jul. 8, 2010

(65) Prior Publication Data
US 2011/0287473 A1    Nov. 24, 2011

(30) Foreign Application Priority Data

Dec. 29, 2008 (FR) ..................................... 08 07473

(51) Int. Cl.
*C07D 209/56* (2006.01)
*C07F 5/02* (2006.01)

(52) U.S. Cl.
CPC ................ *C07F 5/02* (2013.01); *C07D 209/56* (2013.01)

USPC ......................................................... 548/405

(58) Field of Classification Search
USPC .............. 435/23; 530/409; 536/23.1; 546/12; 548/229; 544/229
See application file for complete search history.

(56) References Cited

U.S. PATENT DOCUMENTS 8,476,461 B2 * 7/2013 Ulrich et al. ................... 548/405

FOREIGN PATENT DOCUMENTS

| WO | 2006/087459 | | 8/2006 |
| WO | WO 2006/087459 | * | 8/2006 |

OTHER PUBLICATIONS

Haugland, Richard P.; Handbook of Fluorescent probes and Research products (2002), ISBN 0-9710636-0-5.*
March, Jerry; Advanced Organic Chemistry (1992) Wiley and sons, ISBN 0-471-60180-2.*
Brazil, Melanie I. et al; "Effect of incorporation of immunoglobulin G and complement component C1q on uptake and degradation of alzheimer's disease amyloid fibrils by microglia." J. Biol. Chem. (2000) 275(22) p. 16941-19647.*

* cited by examiner

*Primary Examiner* — Maury Audet
*Assistant Examiner* — Fred Reynolds
(74) *Attorney, Agent, or Firm* — Morgan, Lewis & Bockius LLP

(57) ABSTRACT

The invention relates to novel fluorescent compounds derived from non-fluorinated dipyrromethene-boron, to a method for preparing same and to the use thereof for the fluorescent marking of biological molecules. The invention also relates to biological molecules marked with said fluorescent compounds, and to the use thereof in detection methods such as medical diagnosis methods. More particularly, the detection methods of the invention are particularly useful for diagnosing neurodegenerative diseases such as Alzheimer's disease.

12 Claims, 5 Drawing Sheets i) NaOH, H₂O, EtOH

A

B

```
                           SEQUENCE LISTING

<160> NUMBER OF SEQ ID NOS: 2

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 42
<212> TYPE: PRT
<213> ORGANISM: Homo sapiens

<400> SEQUENCE: 2

Ala Ile Val Val Gly Gly Val Met Leu Gly Ile Ile Ala Gly Lys Asn
1               5                   10                  15

Ser Gly Val Asp Glu Ala Phe Phe Val Leu Lys Gln His His Val Glu
            20                  25                  30

Tyr Gly Ser Asp His Arg Phe Glu Ala Asp
        35                  40
```

FLUORESCENT BORON-SUBSTITUTED DIPYRROMETHENES AND USE THEREOF FOR DIAGNOSIS

RELATED APPLICATIONS

The present application is a U.S. National Phase Application of International Application No. PCT/FR2009/001486 (filed Dec. 28, 2009) which claims priority to French Application No. 087473 (filed Dec. 29, 2008) which are hereby incorporated by reference in their entirety.

SEQUENCE LISTING SUBMISSION VIA EFS-WEB

A computer readable text file, entitled "045636-5169_SequenceListing.txt," created on or about Jun. 23, 2011, with a file size of about 2 kb contains the sequence listing for this application and is hereby incorporated by reference in its entirety.

The present invention relates to novel fluorescent compounds, non-fluorinated dipyrromethene-boron derivatives, a method for preparation of same and the use thereof for the fluorescent labeling of biological molecules. The invention further relates to biological molecules labeled with said fluorescent compounds and to the use thereof in detection methods such as medical diagnostic methods; in particular, the detection methods according to the invention are found to be particularly useful for the diagnosis of neurodegenerative diseases such as Alzheimer's disease.

Fluorescent markers are often used for detecting and/or estimating biological molecules in the fields of immunology, molecular biology, medical diagnosis or again DNA chips.

Among the many compounds from the prior art usable as fluorescent markers, the difluorides of dipyrromethene-borons (hereinafter designated by DFMB) can in particular be cited. The U.S. Pat. No. 4,774,339, U.S. Pat. No. 5,187,288 and U.S. Pat. No. 5,451,663 describe compounds derived from DFMB containing fluorescent functional groups which can be used for labeling biological molecules or polymers.

However, the DFMB derivatives are chemically unstable; thus, in a basic medium or in the presence of nucleophiles such as amines or alcoholates, the fluorine atoms of these compounds are readily replaced.

The international patent applications WO 2006/087459 and WO 2006/087458 describe compounds derived from non-fluorinated dipyrromethene-borons. These compounds exhibit better chemical stability than the DFMB derivatives; in particular, they are resistant to the basic conditions utilized particularly for the deprotection of groups of the carbamate type (for example Fmoc) during automated peptide syntheses.

However, the need remains to have available fluorescent compounds exhibiting:
  further improved chemical stability;
  a high fluorescence quantum yield and high molar extinction coefficients;
  excitation and emission wavelengths which can be controlled; and
  a functional group enabling easy grafting onto biological molecules.

It is this that the applicant has achieved by developing novel fluorescent compounds of general formulae (I) which are non-fluorinated dipyrromethene-boron derivatives having a carbonyl function making it possible to graft them onto biological molecules. The compounds of general formula (I) are chemically more stable than the standard fluorophores such as fluorescein, rhodamines and difluoroboradiaza-indacenes; in addition, these compounds are resistant to the various reagents utilized in the solid support synthesis of peptides or oligonucleotides and are therefore particularly suitable for the labeling of amino acids or nucleotides.

In the context of the invention, biological molecule is understood to mean an amino acid, a polypeptide, a protein, biotin or derivatives or structural analogs thereof, a nucleotide or a nucleic acid (RNA, DNA).

A fluorophore (also referred to as a fluorescent compound or marker) is a compound containing a functional group capable of absorbing light energy at one wavelength (known as the excitation or absorption wavelength) and of releasing all or part of the absorbed energy by emission of light at a wavelength (known as the emission wavelength) greater than or equal to the absorption wavelength; a fluorophore can be covalently linked to a molecule such as a biological molecule.

In general, a molecule is said to be labeled when it contains at least one detectable atom or group of atoms, such as a radioactive atom or group, a chromophore or a fluorophore.

In the context of the present invention, unless otherwise stated, a molecule is said to be labeled when it is covalently linked to a fluorophore.

Labeling is understood to mean the process consisting in covalently linking a fluorophore to a biological molecule; the biological molecule is preferably an amino acid or a nucleotide, the fluorophore then being linked to the side-chain of the amino acid or the nucleotide.

A carbonyl function is a functional group of the following structure:

present for example in a carboxylic acid, an ester, an amide or a thioester. In the context of the present invention, the carbonyl function of the compounds of general formula (I) is defined by the group —(Ar)$_m$—CO—Z where Ar, m and Z are defined below.

The invention thus more particularly relates to the compounds of general formula (I):

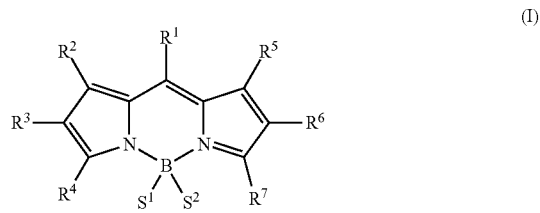

wherein:
  $R^1$ is selected from the group made up of —Ar—CO—Z, a hydrogen atom (—H), -L-H, -G and -L-G,
  where Ar, Z, L and G are defined below,
  $R^3$, $R^4$, $R^6$ and $R^7$ are selected independently of each other from the group made up of —(Ar)$_m$—CO—Z, a hydrogen atom (—H), -L-H, -G and -L-G,
  where m is 0 or 1,
  it being understood that only one of the substituents $R^1$, $R^3$, $R^9$, $R^6$ and $R^7$ is —Ar—CO—Z or —(Ar)$_m$—CO—Z; preferably $R^1$ is —Ar—CO—Z, $R^2$ and $R^5$, the same or different, are selected independently of each other from the group made up of a hydrogen atom (—H), -L-H, -G and -L-G,
where L and G are defined below,
$S^1$ and $S^2$ are hydrophilic groups, the same or different, of formula —C≡C-L'-A;
wherein L' and A are defined below,
Ar is selected from a $C_5$-$C_{14}$ arylene or heteroarylene on which the group —CO—Z is in the ortho, meta or para position, preferably para; Ar is preferably a benzene, naphthalene, anthracene, pyrene, pyridine, pyrimidine, thiophen or pyrrole group;
Z is a group enabling the grafting of the compound of general formula (I) onto a biological molecule; in particular, Z is selected from an —OH, —O-succinimide, —O-maleimide, —N-glycine, —N-lysine, —Y-L"—$NH_2$, —Y-L"—COOH or —Y-L"-SH group where Y is selected from N and O atoms and L" is defined below;
L and L" are selected independently of each other from a single bond, an optionally branched $C_1$-$C_{10}$, preferably $C_1$-$C_6$, carbon chain, a $C_6$-$C_{16}$ arylene on which the groups —H or -G for L and —$NH_2$, —COOH or —SH for L" are in the ortho, meta or para position, preferably para, a $C_2$-$C_4$ alkenylene, a $C_2$-$C_4$ alkynylene, a linear or branched $C_1$-$C_{20}$ carbon chain interrupted by 1 to 10 oxygen atoms, a linear or branched saturated $C_1$-$C_{20}$ carbon chain interrupted by one to four amide functions —CO—NH—, a nucleotide segment and/or a segment of sugars;
G is selected from the group made up of succinimidyl ester, sulfo-succinimidyl ester, isothiocyanate, isocyanate, iodoacetamide, male imide, sulfonyl halides, phosphoramidites, $C_2$-$C_5$ alkylimidates, $C_6$-$C_{10}$ arylimidates, acid halides, preferably acid chlorides and acid bromides, hydrazines substituted with a $C_1$-$C_4$ alkyl, hydroxylamines substituted with a $C_1$-$C_4$ alkyl, carbodiimides and perfluoro-phenols;
L' is selected from a single bond, a $C_1$-$C_{10}$ alkenylene or a linear or branched saturated $C_1$-$C_{20}$ carbon chain interrupted by 1 to 10 oxygen atoms;
A represents a group selected from a $C_1$-$C_4$ alkyl, preferably methyl, a phosphate group or a sulfonate group.
Preferably, A is a methyl, a propyl sulfonate, an ethyl sulfonate or a methyl-phosphate.
The preferred $C_6$-$C_{16}$ arylene groups are selected from benzene, naphthalene and anthracene.
In the invention, the words "$C_1$-$C_4$ alkyl" are used to designate a linear or branched hydrocarbon radical or a cycloalkyl containing from 1 to 4 carbon atoms; for example a methyl, a propyl, an n-butyl, an isopropyl . . . can be cited.
In the invention, "$C_2$-$C_4$ alkenylene" is understood to mean a linear carbon chain of 2 to 4 carbon atoms containing a double bond between two carbon atoms.
In the invention, "$C_2$-$C_4$ alkynylene" is understood to mean a linear carbon chain of 2 to 4 carbon atoms containing a triple bond between two carbon atoms.
In the invention, "$C_2$-$C_{10}$ alkenylene" is understood to mean a linear carbon chain of 2 to 10 carbon atoms containing at least one double bond between two carbon atoms.
Preferably, in the context of the invention, the linear or branched saturated $C_1$-$C_{20}$ carbon chain interrupted by 1 to 10 oxygen atoms is a poly(ethylene oxide) or a poly(propylene oxide), the unit whereof repeats between one and six times.
Nucleotide segment is understood to mean a linear chain containing one or more nucleotides.
Sugar segment is understood to mean a linear chain containing one or more sugar units.

The selection of the radicals $R^1$ to $R^7$ makes it possible to modify the properties of the compound, such as for example its fluorescence emission wavelength, its fluorescence quantum yield, its solubility and its dipole moment.
A particular family of compounds according to the invention comprises the symmetrical compounds of general formula (I), that is to say in which $R^2$ and $R^5$ are identical, $R^3$ and $R^6$ are identical, $R^4$ and $R^7$ are identical and $S^1$ and $S^2$ are identical, in which case the carbonyl function —Ar—CO—Z is borne by $R^1$.
Hereinafter, the compounds of general formula (I) are also designated by the formula P—$(Ar)_m$—CO—Z where P represents the whole of the compound of general formula (I) with the exception of the substituent $R^1$ or $R^3$ or $R^4$ or $R^6$ or $R^7$ which is the group —Ar—CO—Z or —$(Ar)_m$—CO—Z, and where Ar, m and Z have the same definitions as above.
The compounds of general formula (I), in addition to enabling easy grafting onto biological molecules, exhibit numerous advantages:
they emit with strong fluorescence intensity and they do not lose this intensity when they are attached to a biological molecule such as a protein;
they are chemically resistant to the steps of solid support synthesis during the preparation of polypeptides or polynucleotides;
they do not disrupt the properties of the biological molecules to which they are attached.
The synthesis of compounds P—$(Ar)_m$—CO—Z according to the invention is effected from a synthetic intermediate, a dipyrromethene-boron derivative. This synthetic intermediate is obtained by reacting, with the difluoro compound DFMB, a Grignard organometallic reagent (organomagnesium or organolithium) of formula $S^1$—MgX, $S^1$—LiX, $S^2$—MgX or $S^2$LiX, where X is a halogen atom, under the conditions described in the international patent application PCT WO 2006/087459; this reaction makes it possible to introduce the groups $S^1$ and $S^2$ into the difluoro compound DFMB.
This synthetic intermediate has the formula P—$(Ar)_n$-Q, where P, m and Ar are as defined for the formula (I) and Q is selected from a halogen atom, in particular I, Br or Cl; an —O-triflate group (triflate has the formula —O—$SO_2$—$CF_3$ and is also designated by Tf), an —O-tosylate group (tosylate has the formula —O—$SO_2$—$C_6H_6$—$CH_3$ and is also designated by Ts) or an —O— mesylate group (mesylate has the formula —O—$SO_2$—$CH_3$ and is also designated by Ms).
Starting from this synthetic intermediate P—$(Ar)_m$-Q, the radical -Q is transformed into a carbonyl function by reaction with a source of carbon monoxide or with carbon monoxide, in the presence:
of a nucleophile selected depending on the nature of the desired carbonyl function: water to obtain a carboxylic acid, an alcohol to obtain an ester, an amine to obtain an amide and a thiol to obtain a thioester, and
of a palladium-based catalyst, for example $Pd(PPh_3)_2Cl_2$.
The scheme for this synthesis is shown in FIG. 1.
The carbon monoxide used in this reaction can be unlabeled, labeled with an atom of $^{13}C$ with a labeling ratio controllable from 1 to 99% for NMR monitoring, or labeled with a $^{14}C$ atom for radioactive monitoring; such labeling enables supplementary monitoring of the biological molecules labeled with the fluorescent compound (I) according to the invention.
It is necessary to introduce the carbonyl function —CO—Z into the synthetic intermediate P—$(Ar)_m$-Q already containing the groups $S^1$ and $S^2$ on the boron; in fact, the presence of a carbonyl function is not compatible with the use of an organo-metallic compound necessary for the addition of $S^1$ and $S^2$.

One particular example of preparation of compounds of general formula (I) where the carbonyl function is $R^1$ is illustrated in example 1.

Similarly, carbonyl functions can be introduced directly at the position $R^3$ or $R^4$ or $R^7$ or $R^6$ if these positions possess a group -Q as defined above, by means of a coupling catalyzed by palladium in the presence of carbon monoxide or of any other source of carbon monoxide.

Thus, one subject matter of the present invention relates to a process for preparation of compounds of general formula (I), characterized in that it comprises the transformation of the synthetic intermediate P—$(Ar)_m$-Q into a compound of general formula (I) by reaction with carbon monoxide in the presence of a nucleophile selected from water, an alcohol, an amine or a thiol and of a palladium-containing catalyst; said synthetic intermediate is such that P is a group of structure identical to that of the compound of general formula (I) to be prepared with the exception of the radical $R^1$ or $R^3$ or $R^4$ or $R^6$ or $R^7$ depending on which is the group —Ar—CO—Z for $R^1$ or —$(Ar)_m$—CO—Z for $R^3$ or $R^4$ or $R^6$ or $R^7$, Ar is as defined for the formula (I), m is 0 or 1, it being understood that m is 1 if $R^1$ is the carbonyl function —Ar—CO—Z and Q is selected from a halogen atom, an —O-triflate, an —O-tosylate or an —O-mesylate. In a favored embodiment, $R^1$ is —Ar—CO—Z.

Also a subject matter of the present invention is the use of a compound of general formula (I) as a fluorescent marker.

Owing to its carbonyl function, the compound of formula (I) can easily be grafted onto a biological molecule such as an amino acid, a protein, biotin or one of the derivatives or structural analogs thereof or a nucleotide.

Also, according to another of its subject matters, the present invention relates to a labeled biological molecule of general formula (II) (hereinafter referred to as "labeled biological molecule"):

P—$(Ar)_m$—CO—$(X)_n$-T        (II)

wherein:

P, Ar and m are as defined above and m is 0 or 1, it being understood that m is 1 if the group —$(Ar)_m$—CO—$(X)_n$-T is substituted on $R^1$;

X is a spacer bearing a carboxyl, amine or thiol function; it is for example a chain comprising between one and three amino acids, or again a $C_1$-$C_6$ alkylene which can be interrupted by 2 or 3 oxygen atoms and which binds covalently to the fluorophore and to the biological molecule by means of an amide, ether, ester or thioester function or a disulfide bridge;

n is a whole number equal to 0 or 1, and

T is a biological molecule.

In the context of the invention, the spacer serves to distance the biological molecule T from the fluorophore P. Preferably, the spacer is chemically inert, in other words it does not react with any of the groups which it distances; in particular, it does not affect the fluorescence of the fluorophore nor the biological activity of the biological molecule.

As the biological molecule, T is selected from a natural or synthetic amino acid, a polypeptide, a protein, biotin or derivatives or structural analogs thereof, a nucleotide or a nucleic acid (RNA, DNA).

When T is an amino acid, it is selected from alanine, arginine, asparagine, aspartate or aspartic acid, cysteine, glutamate or glutamic acid, glutamine, glycine, histidine, isoleucine, leucine, lysine, methionine, phenylalanine, proline, serine, threonine, tryptophan, tyrosine and valine. Preferably, T is lysine or glycine.

When T is a nucleotide, it is selected from the ribonucleotides such as adenosine, uridine, guanosine, cytidine or ribothymidine or the desoxyribonucleotides such as desoxyadenosine, desoxyuridine, desoxyguanosine, desoxycytidine or desoxy-ribothymidine.

The labeled biological molecules are prepared according to the methods that follow.

When T is an amino acid or a protein, the preparation of the labeled biological molecule of general formula (II) is effected from a compound of general formula (I) functionalized with a group Z bearing a carboxylic acid; said compound (I) is (i) transformed into a hydroxysuccinimide or tetrafluorophenyl ester, then (ii) reacted with the amino acid or protein (Guide to Labeling proteins with Fluorescent Dyes—Note 7.1 http://www.invitrogen.com/site/us/en/home/References/Molecular-Probes-The-Handbook/).

The peptide coupling can also be effected with 1-(3-dimethylaminopropyl)-3-ethylcarbodiimide (EDCI, see example 1).

It can be advantageous in step (ii) to use an amino acid already linked to a protective group such as BOC (t-butoxycarbonyl), Fmoc (9-fluorenylmethyloxy-carbonyl), Bpoc (2-(4-biphenylyl) propyl(2)oxycarbonyl), Nps (2-nitrophenylsulfenyl) or Dts (dithia-succinoyl), the protective group being introduced on the amine function of the amino acid which is involved in the formation of the polypeptide; in fact, thus protected, the labeled amino acid can then be used in a standard technique for solid phase synthesis of peptides (Merrifield, R. B. J. Am. Chem. Soc. 1963, 85, 2149-2154). From this synthesis, a fluorescent polypeptide is obtained on account of the presence of the fluorophore on at least one of its amino acids.

According to one variant of the invention, T is biotin or one of the derivatives or structural analogs thereof. In that case, the preparation of the labeled biological molecule of general formula (II) is effected from a compound of general formula (I) functionalized with a group Z bearing a carboxylic acid; said compound (I) is (i) transformed into an amide by a hydrolysis reaction with an aliphatic diamine which can be 1,6-diaminohexane, 1,3-diaminopropane or 1,2-diaminoethane, then (ii) reacted, by any standard method known to those skilled in the art, with biotin or one of the derivatives or structural analogs thereof possessing a free carboxylic acid function.

According to another variant of the invention, T is a nucleotide. The preparation of the labeled biological molecule of general formula (II) is then effected from a compound of general formula (I) functionalized with a group Z bearing a carboxylic acid; said compound (I) is reacted, by any standard method known to those skilled in the art, with a modified nucleotide with a free amine function.

This labeled nucleotide is then advantageously utilized for the synthesis of labeled oligonucleotides.

There are several techniques for the synthesis of oligonucleotides; the solid support oligonucleotide synthesis inspired by that proposed by Merrifield for peptide synthesis can in particular be cited, or again the synthesis of oligonucleotides by the phosphoramidite method (Matteucci, M. D.; Caruthers, M. H. Tetrahedron Lett. 1980, 21, 719-722; Matteucci, M. D.; Caruthers, M. H. J. Am. Chem. Soc. 1981, 103, 3185-3191).

The interaction of the labeled biological molecule with a ligand leads to a change in the fluorescence emission spectrum of said molecule; the development of detection methods derives from this property.

Another advantage deriving from this property is that the implementation of the detection methods can take place with the fluorophore according to the invention alone and does not require the combination of several fluorophores or a fluorophore-fluorescence suppressor couple, as is for example the case for techniques such as the FRET technique for measurement of the interaction between proteins (for Fluorescence Resonance Energy Transfer, see Lopper et al., *Protein-protein interactions: identification,* 2007, Encyclopedia of Life Science) or real time PCR (Poitras et al., *La PCR en temps réel: principes et applications,* 2002, Reviews in Biology and Biotechnology, vol. 2, N°2, p. 2-11); however that does not prevent the use of the fluorophores according to the invention in these techniques.

In the context of the invention, a ligand is a molecule the presence or absence whereof in a sample is to be detected; the biological molecule is selected for its property of interacting with the ligand.

The emission spectrum of a fluorophore can be measured by any standard method known to those skilled in the art. Preferably, the fluorescence emission spectrum will be measured by means of a spectrofluorimeter or a microscopy device equipped with a spectral detector; the spectrum is represented on a graph with the wavelength on the x-axis and the light intensity on the y-axis.

It is thus possible to measure the anisotropy index of the fluorescence spectrum of a labeled biological molecule under different conditions (in the presence or absence of a test sample).

Anisotropy index of a spectrum (also referred to as the spectral index or deformation index) is understood to mean an index representing the asymmetry of the spectrum in relation to the position of the main fluorescence emission peak.

To determine the anisotropy index of the spectra measured, the spectra are subjected to an analysis which consists in breaking them down into component Gaussian curves by deconvolution using a non-linear regression method. The characteristics of these Gaussian curves (position of the peak, amplitude, area and dispersion) are calculated:
- the position of the peak corresponds to the wavelength at which a light intensity maximum can be observed;
- the amplitude is the light intensity of the peak;
- the area is the integral of the light intensity under the curve;
- the dispersion is the half-height width of the curve expressed in wavelength.

Within the same spectrum, the ratio of the amplitude or of the area of the two main Gaussians makes it possible to define the deformation index of the fluorescence spectrum as a function of the conditions under which the spectrum is recorded. The changes in the value of the deformation index of the spectrum measured in the presence or absence of a sample make it possible to detect the presence of a ligand and to evaluate the proportion thereof.

In one variant, the anisotropy of the spectrum can also be measured by means of band pass optical filters. The deformation index of the spectrum will then be evaluated using the ratio of the fluorescence intensities measured by means of different band pass filters.

Thus, according to another subject matter thereof, the invention relates to a method for detection of the ligand of a labeled biological molecule of general formula (II) in a sample comprising the following steps:

a) measurement of the fluorescence emission spectrum of the test sample alone; the spectrum obtained is designated "base line";

b) measurement of the fluorescence emission spectrum of the labeled biological molecule in solution; subtraction of the base line from the spectrum obtained and calculation of the deformation index;

c) incubation of said labeled biological molecule in solution with the test sample and obtention of a mixture;

d) measurement of the fluorescence emission spectrum of the mixture obtained in step c); subtraction of the base line from the spectrum obtained and calculation of the deformation index;

e) comparison of the deformation indices calculated in steps b) and d) and detection of the interaction between the ligand and the labeled biological molecule when said indices are different.

Preferably, in step b), the biological molecule is in solution in a solution which has the same composition as the solution wherein the fluorescence spectrum of the labeled molecule is measured in the presence of the biological sample.

According to one variant of the invention, the detection method also makes it possible to, quantify the ligand in the sample. In order to do this, a calibration curve of the value of the deformation index of the spectrum as a function of the quantity of ligand is created beforehand.

In addition, if the ligand can exhibit different conformations—which can be the case for a peptide, the three-dimensional conformation whereof can vary depending on its environment—the fluorescence spectrum of the labeled biological molecule complexed with the ligand will be different depending on the conformation of the ligand; this property makes it possible to implement a method for qualitative detection of a ligand.

The sample can be of biological origin, that is to say that it represents all or part of an organ, a tissue, a cell, a microorganism, etc.

The sample can also be of any other nature, it can for example, and without this being limiting, be a food where it is desired to test for the absence of contaminants such as undesirable or even pathogenic microorganisms, toxins or pollutants such as pesticides, etc.

The implementation of the detection method according to the invention can also be useful for diagnosing a disease.

Thus, a method for diagnosis of neurodegenerative diseases such as Alzheimer's disease has been developed.

The general increase in longevity favors the prevalence of neurodegenerative diseases and, in particular, of Alzheimer's disease. These conditions constitute a major social and economic problem for modern society. Clinical examination combined with medical imaging and neuropsychological tests only enable late diagnosis in the terminal phase of the disease and the definitive diagnosis can only be obtained by post-mortem examination of the cerebral tissues, which is not satisfactory. Thus, various routes have been explored for identifying a peripheral biological marker which would enable a non-invasive diagnosis of the disease.

It has been demonstrated that the erythrocytes are altered in Alzheimer's disease; this alteration is observed as an abnormal conformation of protein kinase C which can be caused by the deregulation of the intracellular calcium concentration (Janoshazi et al. *Neurobiol. Aging* 2006, 27: 245-251).

In addition, it has been shown that human beta-amyloid peptide, produced in the nerve tissues and in the blood in the course of Alzheimer's disease, could interact with the surface of erythrocytes (Mattson M P et al. *Brain Res* 1997, 771: 147-153), modifying their calcium homeostasis.

Tests performed in the context of the invention show that living cells, such as erythrocytes, previously placed in the presence of low concentrations of unlabeled beta-amyloid peptide 1-42, are capable of subsequently binding a beta-amyloid peptide bearing a fluorophore described in the invention; this binding is accompanied by a specific deformation of the fluorescence spectrum of the fluorophore, making it possible to evaluate the concentration of unlabeled beta-amyloid peptide 1-42 to which the cells were previously exposed. It is therefore possible to quantify the human beta-amyloid peptide 1-42 circulating in an individual.

More specifically, the method of diagnosis of Alzheimer's disease implements the detection method according to the invention; it makes it possible to evaluate the quantity of beta-amyloid peptide 1-42 in a sample where:

the biological sample contains erythrocytes, for example, blood; and the labeled biological molecule is such that T is a peptide derived from beta-amyloid peptide 1-42.

Beta-amyloid peptide 1-42 is the peptide of sequence SEQ ID No.: 1.

Derivative of beta-amyloid peptide 1-42 is understood to mean a peptide, one or more of the amino acids whereof have been replaced by the same amino acid labeled with a fluorescent compound of general formula (I) according to the invention; this derivative can also contain one or more insertions of a labeled amino acid in any part of its chain.

By way of example, the preparation of a derivative of beta-amyloid peptide 1-42 is described in example 1 and results in the following peptide: H-Asp-Ala-glu-Phe-Arg-His-Asp-Ser-Gly-Tyr-Glu-Val—His-His-Gln-Lys*-Leu—Val-Phe-Phe-Ala-Glu-Asp-Val-Gly-Ser-Asn-Lys-Gly-Ala-Ile—Ile-Gly-Leu-Met-Val-Gly-Gly-Val—Val-Ile-Ala-OH (SEQ ID No.: 1), where the fluorophore is borne by the lysine in position 16.

Amino acids other than lysine can be labeled and utilized to prepare the derivative of the beta-amyloid peptide 1-42; these are preferably amino acids having an amine or carboxylic acid function in their side-chain.

The value of the deformation indices of the fluorescence spectra measured in the sample, then the comparison with a calibration curve, make it possible to evaluate the proportion of beta-amyloid peptide 1-42 present in the test sample.

For the implementation of this diagnostic method, the calibration curve is generated using human erythrocytes derived from a healthy subject and preincubated for 18 hours in the presence of increasing concentrations of beta-amyloid peptide 1-42. Then step e) of the method according to the invention consists in comparing the deformation index of the spectrum obtained in step d) with the calibration curve.

Thus, this method makes it possible to evaluate the quantity of circulating beta-amyloid peptide 1-42 while overcoming the difficulties of estimation caused by the interaction of this peptide with other soluble proteins such as serum albumin. It constitutes an original means for diagnosis of Alzheimer's disease which is simple, fast and inexpensive. It is also a means for prognosis, for monitoring the efficacy of a treatment against the disease and for development of therapeutic agents with the aid of cell lines or animal models of the disease.

Another embodiment of the method according to the invention enables the identification of a compound capable of interacting with the ligand of a labeled biological molecule; such an embodiment comprises the following steps:

a) measurement of the fluorescence emission spectrum and calculation of the deformation index of the labeled biological molecule in solution;

b) incubation of said labeled biological molecule in solution with a ligand and obtention of a mixture 1;

c) measurement of the fluorescence emission spectrum and calculation of the deformation index of the mixture 1;

d) incubation of said ligand with said test compound, then addition of said labeled biological molecule in solution and obtention of a mixture 2;

e) measurement of the fluorescence emission spectrum and calculation of the deformation index of the mixture 2;

f) detection of the interaction between the ligand and the test compound by comparison of the deformation indices calculated in steps a), c) and e).

Thus implemented, the method makes it possible to identify potential therapeutic agents, or again to measure the efficacy of such an agent in vitro and ex vivo.

The invention also relates to diagnostic kits or sets of reagents for the implementation of the detection method according to the invention. These kits are characterized in that they contain at least one labeled biological molecule of general formula (II) according to the invention, with the appropriate contents and reagents and directions for use.

The invention is now described in more detail with reference to the diagrams and examples that follow. It must however be clearly understood that these examples are given solely by way of illustration of the subject matter of the invention, whereof they in no way constitute a limitation.

Figure 3:
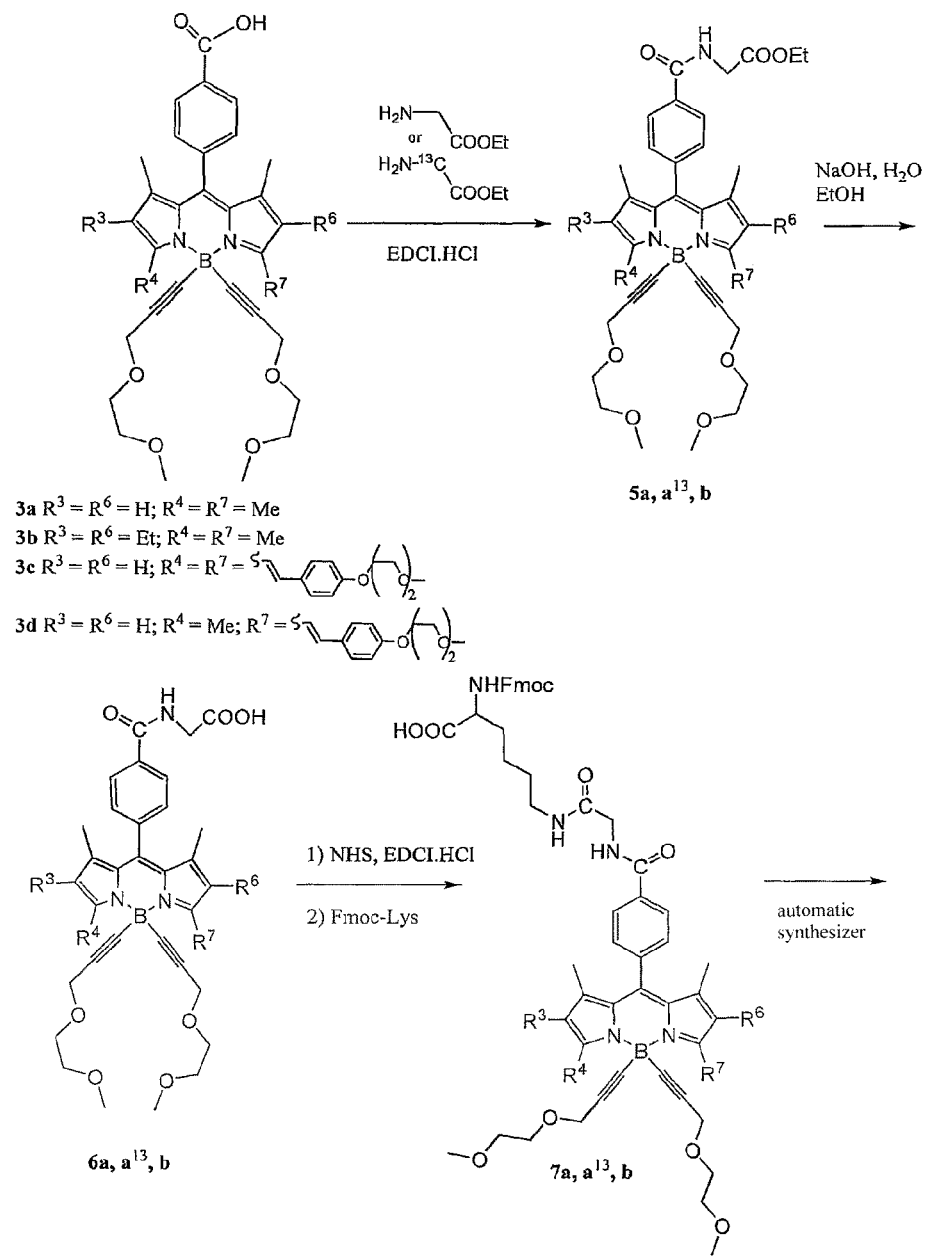

FIG. 3 shows the synthetic scheme leading to the compounds 6a[13]-b and 7a, 7a[13] and b as described in example 1 (EDCI=N-(3-dimethylaminopropyl)-N'-ethylcarbodiimide and NHS=N-hydroxysuccinimide).

Figure 4:
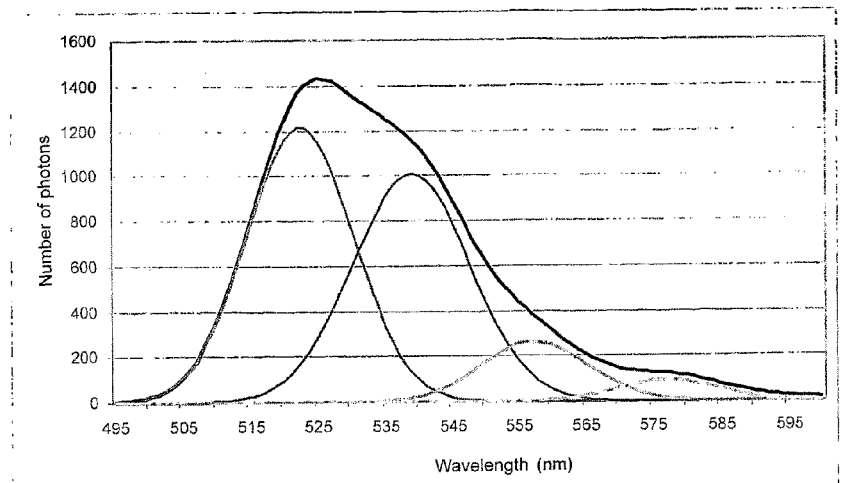
Figure 4:
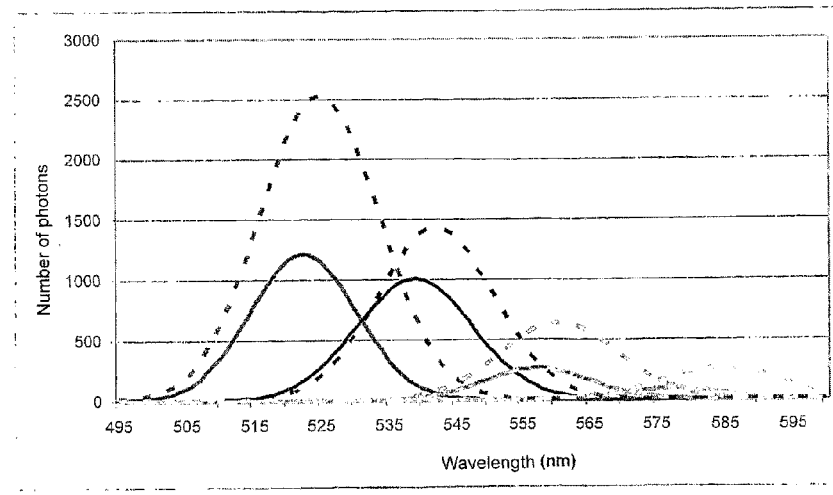

FIG. 4 illustrates the measurement of fluorescence emission spectra under the conditions of example 3. Graph A shows the fluorescence spectrum of the beta-amyloid peptide linked to compound 7a and graph B shows the deconvolution of the fluorescence spectrum of the beta-amyloid peptide linked to compound 7a recorded in the presence of PC12 cells before preincubation (solid lines) and after preincubation (dotted lines) of the cells with the unlabeled beta-amyloid peptide 1-42.

Figure 5:
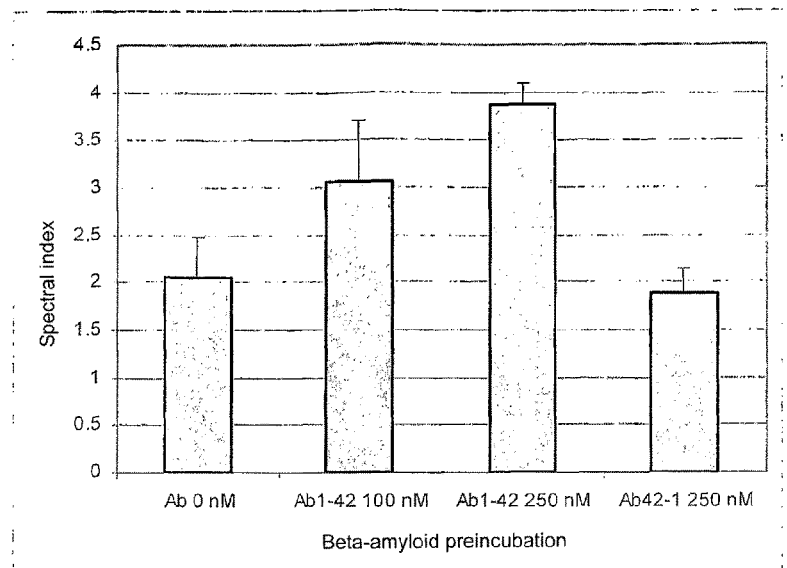

FIG. 5 is the graph showing the values of the spectral index of compound 7a linked to the beta-amyloid peptide 1-42 after preincubation of different concentrations of unlabeled beta-amyloid peptide (Ab) as described in example 4.

Figure 6:
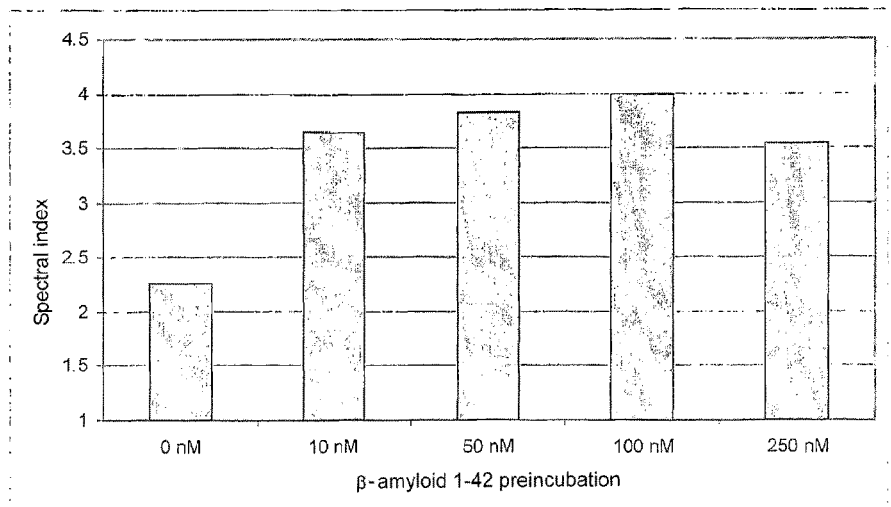

FIG. 6 is a histogram which illustrates the change in the value of the spectral index of the beta-amyloid peptide 1-42 linked to compound 7a in the presence of rat erythrocytes preincubated with the unlabeled beta-amyloid peptide 1-42 as described in example 5.

EXAMPLE 1

Preparation of Compounds of General Formula (I) According to the Invention where $R^1$ is —Ar—Co—Z The compounds 1a-d to 7a-b of this example were selected for their spectral correspondence with the currently most utilized fluorophores with the symbol a: fluorescein, symbol b: rhodamine 6G; symbol c: TMR (tetramethyl rhodamine) and symbol d: TOTO-3.

Figure 1:
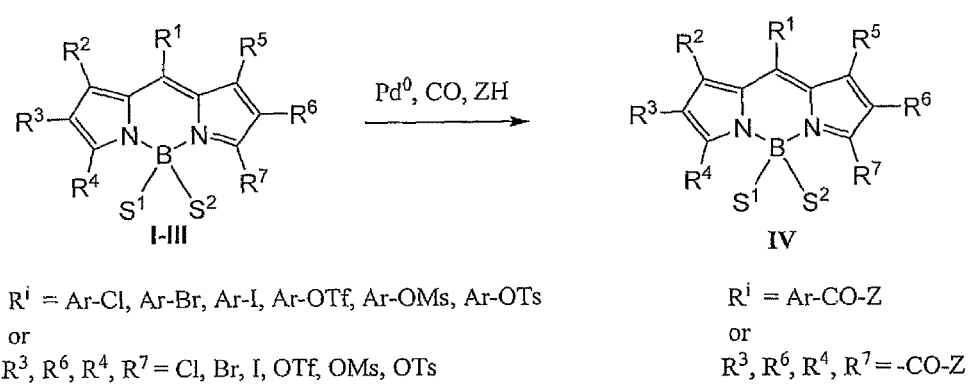
FIG. 1 shows a scheme for the synthesis of the compounds of general formula (I) according to the invention.
Figure 2:
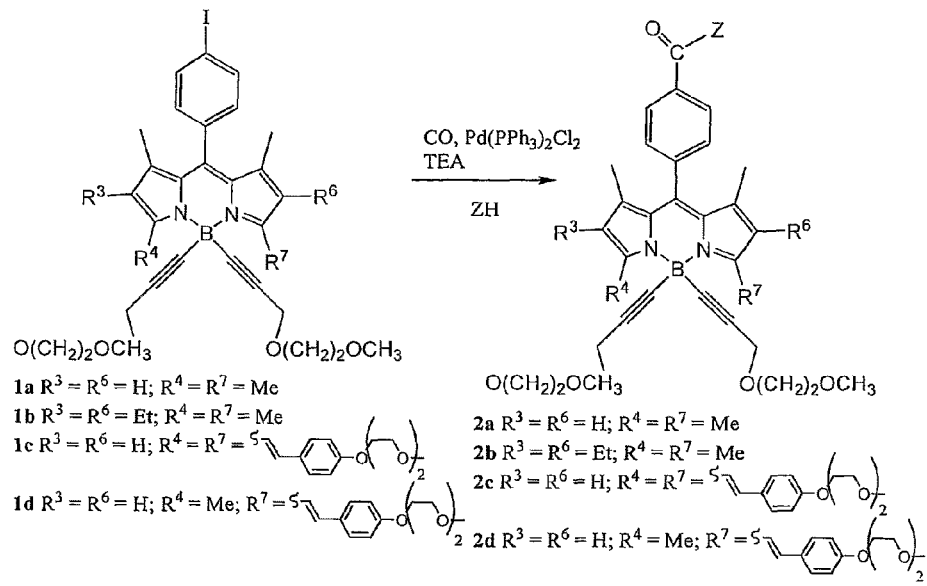
FIG. 2 shows the synthetic scheme leading to the compounds 1a-d to 6a as described in example 1 (TEA=triethylamine).
Figure 2:
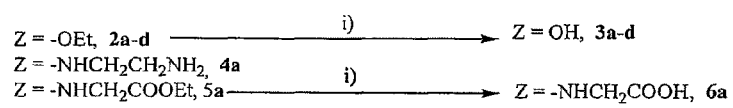

The synthetic scheme leading to compounds 1a-d to 6a is shown in FIG. 2.

The compounds 1a-d are obtained by the action of the methoxyethoxyethynyl organometallic (Grignard reagent) in THF at 60° C. on the corresponding difluoro product (which can be prepared as described in the U.S. Pat. No. 4,744,339) following the operating procedures described in the international patent application WO 2006/087459.

The iodine borne by the compounds 1a-d is next converted to a carbonyl group under an atmosphere of carbon monoxide in the presence of $Pd(PPh_3)_2Cl_2$ catalyst in a mixture of triethylamine and benzene at 70° C.

The selection of the nucleophile utilized makes it possible to obtain directly numerous functional groups which can then be utilized for the coupling onto a biological molecule:

with ethanol, the ethyl esters 2a-d are obtained in very good yields;

by utilizing an aliphatic diamine in excess, compounds of the type 4 can be obtained;

when an amino acid with a free amine and protected at the carboxylic acid function (for example, an ethyl ester of glycine) is used directly, the amino acid can be introduced directly to give compounds of the type 5.

Starting from the compounds 3a-d, the compounds 7a, $a^{13}$, b according to the synthetic scheme shown in FIG. 3 are obtained. The compounds bearing an exponent "$^{13}$" are labeled with $^{13}C$.

The ester function of the compounds 2a-d can be saponified to obtain the corresponding carboxylic acids 3a-d, in the presence of caustic soda in ethanol (see FIG. 2). These carboxylic acids can either be directly utilized for the labeling of biological molecules, or linked to spacers of the amino acid type (grafting using peptide coupling techniques used with the compounds 6a-b below as shown on the synthetic scheme of FIG. 3).

For them to be able to be usable in a peptide synthesizer, the compounds 3a-b are coupled with a glycine ester via a standard peptide synthesis (EDC, DMAP). This step makes it possible if necessary to introduce for example a fragment labeled with a $^{13}C$ atom (compound $5a^{13}$) to enable NMR traceability.

The compounds 5a-b obtained are then saponified to carboxylic acids 6a-b.

The acids 6a-b are transformed into the hydroxysuccinimide esters, which are directly reacted with a lysine-Fmoc.

The compounds 7a-b can be utilized directly to introduce a labeled amino acid Lys into a peptide synthesizer.

Preparation of the Compound 2a

The compound 2a is prepared according to the following reaction scheme:

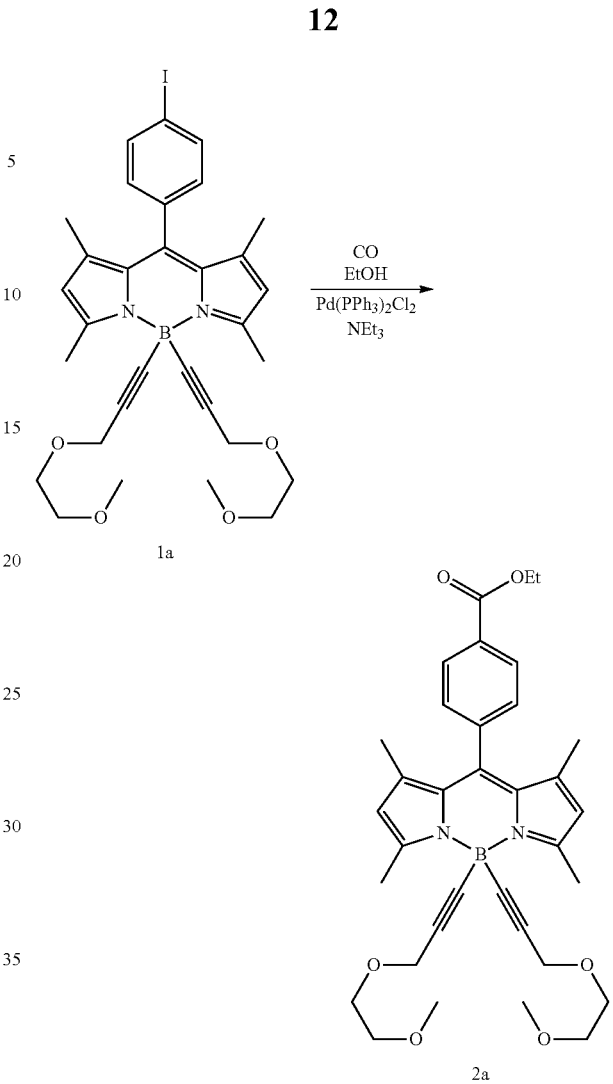

To a solution of compound 1a (235 mg, 0.37 mmol) in 15 mL of benzene were added 1 mL of ethanol (17.2 mmol), 44 mg of palladium bis-triphenylphosphine dichloride (0.07 mmol) and 5 mL of triethylamine. The solution was stirred at 70° C. for one night by "bubbling in" carbon monoxide. The reaction mixture was extracted with dichloromethane and washed with water (3×20 mL). The organic phase was dried over hydrophilic cotton and evaporated. The residue was purified by chromatography on a silica gel column ($CH_2Cl_2$/ MeOH 99:1 or AcOEt/petroleum ether 40:60) to give the compound 2a in the form of an orange powder (210 mg, 97%).

Characterization of the Compound 2a $^1H$ NMR ($CDCl_3$, 400 MHz): δ=1.33 (s, 6H), 1.42 (t, 3H, $^3J$=7.0 Hz), 2.71 (s, 6H), 3.35 (s, 6H), 3.53 (m, 4H), 3.64 (m, 4H), 4.19 (s, 4H), 4.40 (q, 2H, $^3J$=7.0 Hz), 6.00 (s, 2H), 7.78 (AB sys, 4H, $J_{AB}$=8.5 Hz, $v_0$δ=300.4 Hz);

$^{13}C$ NMR ($CDCl_3$, 100 MHz,): δ=14.4, 14.8, 16.1, 59.0, 59.7, 61.4, 68.4, 68.6, 71.8, 90.9, 121.8, 128.6, 129.1, 130.3, 131.0, 140.3, 140.3, 140.9, 155.6, 166.1;

$^{11}B$ NMR ($CDCl_3$, 128.4 MHz): δ=−10.2 (s);

UV-Vis ($CH_2Cl_2$) λ nm (ε, $M^{-1}$ $cm^{-1}$)=500 (90,000), 366 (4900), 308 (7700);

$FAB^+$ m/z: 585.2 ($[M+H]^+$, 100);

Elemental analysis calculated for $C_{34}H_{41}BN_2O_6$: C, 69.86; H, 7.07; N, 4.79. Found: C, 69.77; H, 7.04; N, 4.59.

Preparation of the Compound 2b

The compound 2b is prepared according to the following reaction scheme:

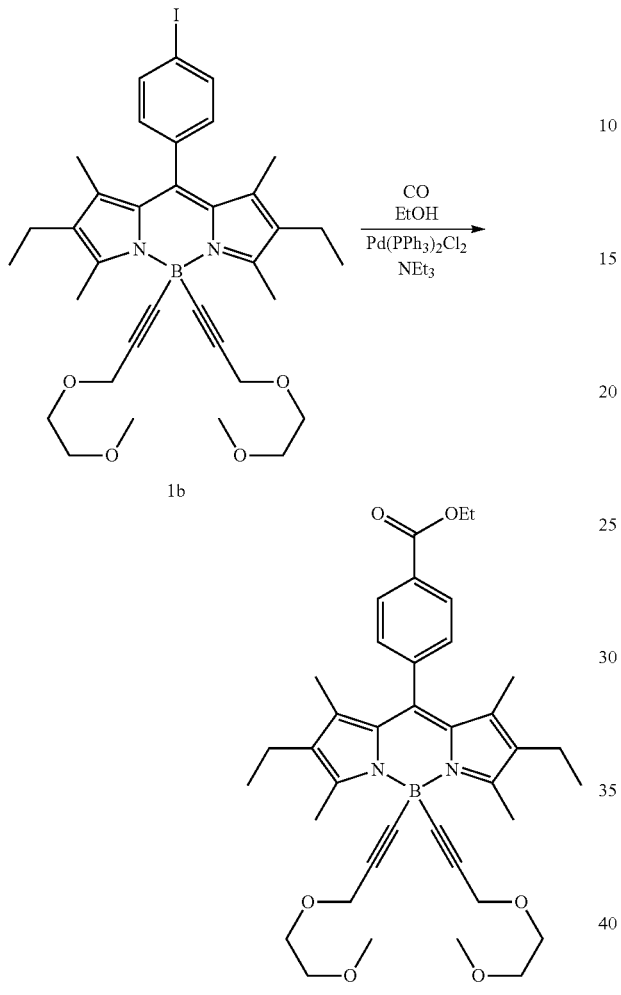

To a solution of compound 1b (980 mg, 1.41 mmol) in 50 mL of benzene were added 3 mL of ethanol (17.2 mmol), 240 mg of palladium bis-triphenylphosphine dichloride (0.07 mmol) and 15 mL of triethylamine. The solution was stirred at 70° C. for one night by "bubbling in" carbon monoxide. The reaction mixture was extracted with dichloromethane and washed with water (3×20 mL). The organic phase was dried over hydrophilic cotton and evaporated. The residue was purified by chromatography on a silica gel column (AcOEt/petroleum ether 20:80; 40:60) to give the compound 2b in the form of an orange powder (895 mg, quantitative).

Characterization of the Compound 2b $^{1}$H NMR (CDCl$_3$ 300 MHz): 0.97 (t, 6H, $^3J$=7.40 Hz), 1.23 (s, 6H), 1.43 (t, 3H, $^3J$=7.10 Hz), 2.31 (q, 4H, $^3J$=7.40 Hz) 2.69 (s, 6H), 3.35 (s, 6H), 3.53 (m, 4H), 3.65 (m, 4H), 4.19 (s, 4H), 4.43 (q, 2H, $^3J$=7.10 Hz), 7.78 (AB sys, 4H, J$_{AB}$=8.19 Hz, $\nu_0\delta$=223.07 Hz);

$^{13}$C NMR (CDCl$_3$, 300 MHz,): δ=12.03, 14.07, 14.41, 14.76, 17.40, 29.78, 59.02, 59.79, 61.37, 68.57, 71.85, 90.67, 128.60, 128.95, 130.19, 130.81, 133.11, 136.02, 138.77, 141.27, 154.05, 166.28.

$^{11}$B NMR (CDCl$_3$, 128.4 MHz): δ=−10.2 (s);

UV-Vis (CH$_2$Cl$_2$) λ nm (ε, M$^{-1}$ cm$^{-1}$)=522 (80,000), 488 (20,000), 381 (6400), 277 (6400).

Preparation of the Compound 2c

The compound 2c is prepared according to the following reaction scheme:

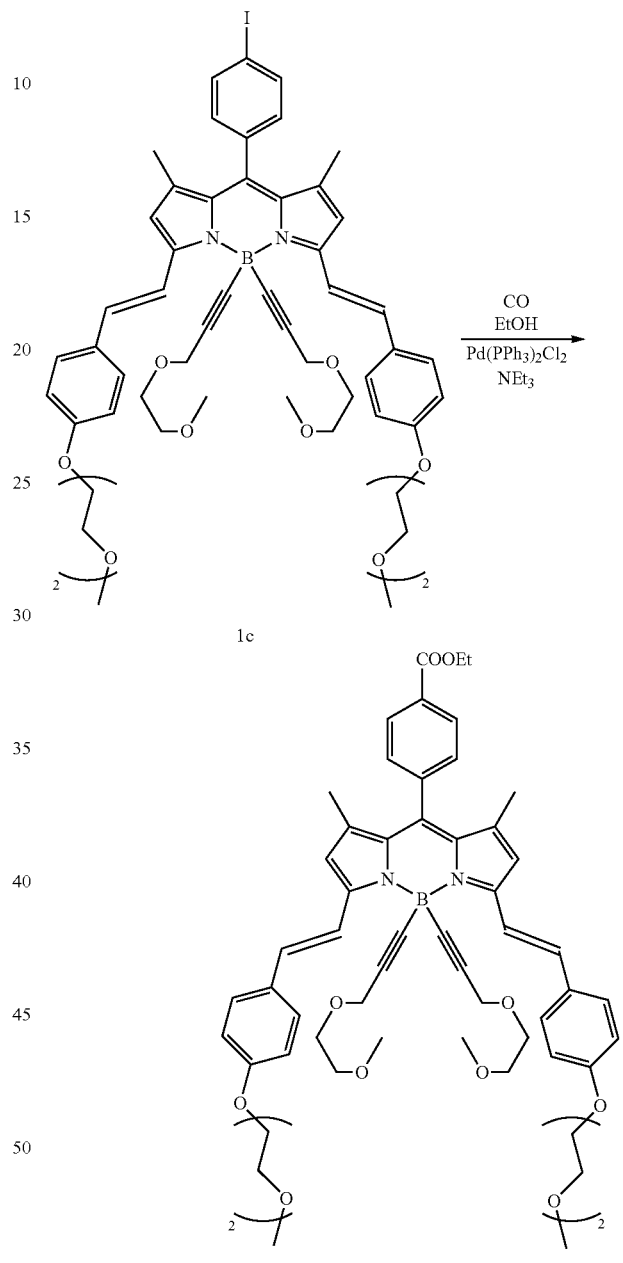

To a solution of compound 1c (100 mg, 0.095 mmol) in 25 mL of benzene were added 1 mL of ethanol, 24 mg of palladium bis-triphenylphosphine dichloride and 5 mL of triethylamine. The solution was stirred at 70° C. for one night by "bubbling in" carbon monoxide. The reaction mixture was extracted with dichloromethane and washed with water (3×10 mL). The organic phase was dried over hydrophilic cotton and evaporated. The residue was purified by chromatography on a silica gel column (AcOEt/petroleum ether 80:20; 100%) to give the compound 2c in the form of a blue powder (88 mg, 92%).

Characterization of the Compound 2c $^1$H NMR (CDCl$_3$ 200 MHz): 1.40 (s, 6H), 1.44 (t, 3H, $^3$J=10.5 Hz) 3.15 (m, 4H), 3.19 (s, 6H), 3.41 (s, 6H), 3.50 (m, 4H), 3.59 (m, 4H), 3.74 (m, 4H), 3.88 (m, 4H), 4.15 (s, 4H), 4.18 (m, 4H), 4.41 (q, 2H, $^3$J=10.5 Hz), 6.62 (s, 2H), 7.27 (AB sys, 8H, J$_{AB}$=8.73 Hz, ν$_0$δ=120.73 Hz), 7.60 (AB sys, 4H, J$_{AB}$=16.26 Hz, ν$_0$δ=192.63 Hz) 7.83 (AB sys, 4H, J$_{AB}$=8.34 Hz, ν$_0$δ=141.89 Hz).

UV-Vis (CH$_2$Cl$_2$) λ nm (ε, M$^{-1}$ cm$^{-1}$)=647 (121,000), 373 (72,800).

Preparation of the Compound 2d

The compound 2d is prepared according to the following reaction scheme:

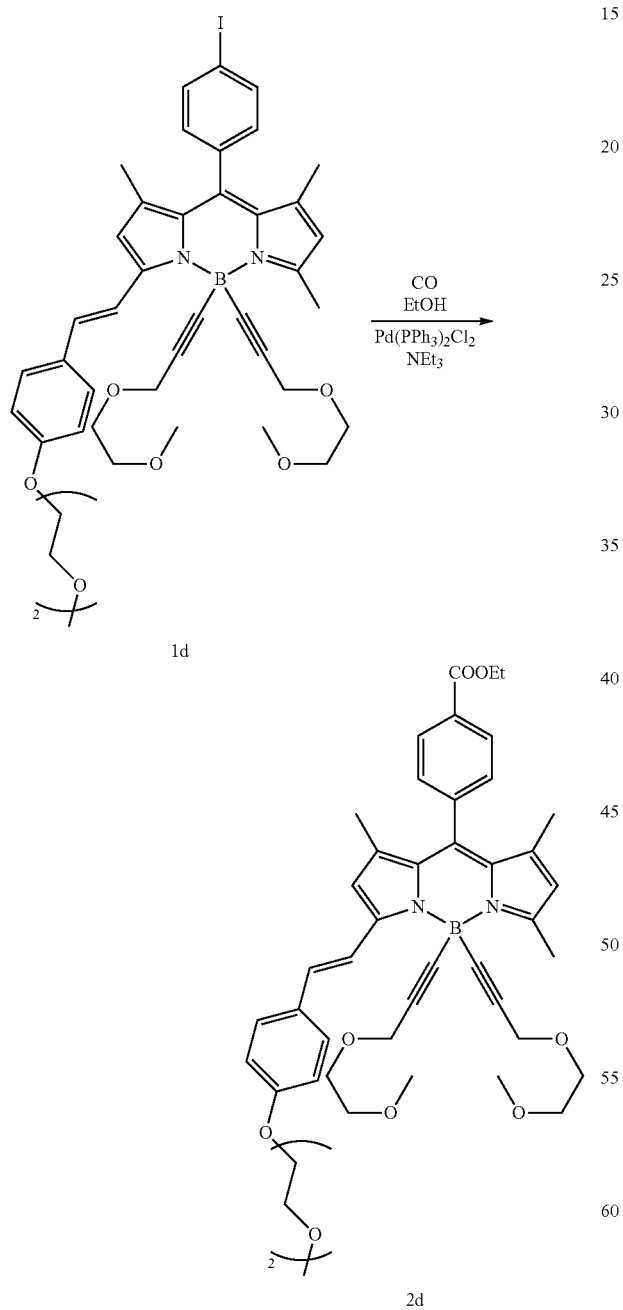

To a solution of compound 1d (100 mg, 0.118 mmol) in 25 mL of benzene were added 2 mL of ethanol, 24 mg of palladium bis-triphenylphosphine dichloride (0.07 mmol) and 5 mL of triethylamine. The solution was stirred at 70° C. for one night by "bubbling in" carbon monoxide. The reaction mixture was extracted with dichloromethane and washed with water (3×10 mL). The organic phase was dried over hydrophilic cotton and evaporated. The residue was purified by chromatography on a silica gel column (AcOEt/petroleum ether 20:80; 40:60) to give the compound 2d in the form of a violet powder (82 mg, 88%).

Characterization of the Compound 2d $^1$H NMR (CDCl$_3$ 300 MHz): 1.35 (s, 3H), 1.38 (s, 3H), 1.43 (t, 3H, $^3$J=7.15 Hz) 2.74 (s, 3H), 3.25 (s, 6H), 3.31 (m, 4H), 3.39 (s, 3H), 3.54 (m, 6H), 3.72 (m, 2H), 3.87 (m, 2H), 4.18 (m, 4H), 4.43 (q, 2H, $^3$J=7 Hz), 6.02 (s, 1H), 6.59 (s, 1H), 7.22 (AB sys, 4H, J$_{AB}$=8.67 Hz, ν$_0$δ=180.18 Hz); 7.58 (AB sys, 2H, J$_{AB}$=16.29 Hz, ν$_0$δ=297.72 Hz), 7.85 (AB sys, 4H, J$_{AB}$=7.99 Hz, ν$_0$δ=226.28 Hz).

Preparation of the Compound 3a

The compound 3a is prepared according to the following reaction scheme:

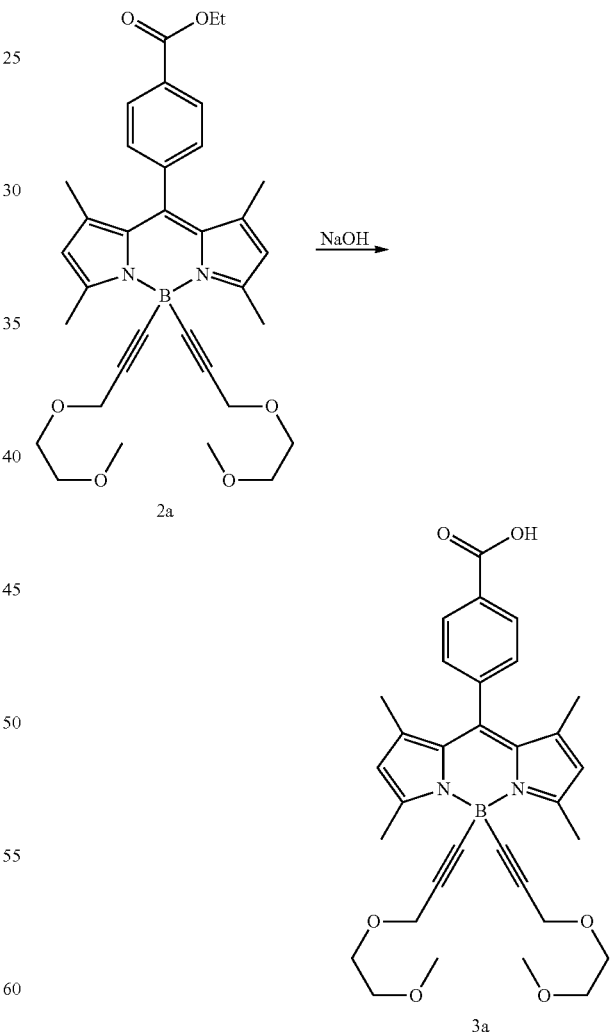

To a solution of compound 2a (210 mg, 0.36 mmol) in 20 mL of ethanol were added 215 mg of caustic soda (5.39 mmol). The solution was stirred for 3 hours at ambient temperature. 30-40 mL of ethyl acetate were added. The organic phase was extracted with water (3×20 mL). The aqueous phases were combined and acidified to pH 1-2 with 1M HCl solution.

The aqueous phase was extracted with dichloromethane. The organic phase was dried over hydrophilic cotton, then evaporated to dryness to give the compound 3a in the form of an orange powder (190 mg, 95%).

Characterization of the Compound 3a

UV-Vis ($CH_2Cl_2$) λ nm ($\epsilon$, $M^{-1}$ $cm^{-1}$)=501 (72,800), 366 (4000), 307 (6400);

UV-Vis (PBS buffer) λ nm ($\epsilon$, $M^{-1}$ $cm^{-1}$)=494 (71,500), 364 (3900), 307 (4900).

Preparation of the Compound 3b

The compound 3b is prepared according to the following reaction scheme:

UV-Vis (PBS buffer) λ nm ($\epsilon$, $M^{-1}$ $cm^{-1}$)=517 (65,000), 378 (3600), 320 (5000);

Preparation of the Compound 3c

The compound 3c is prepared according to the following reaction scheme:

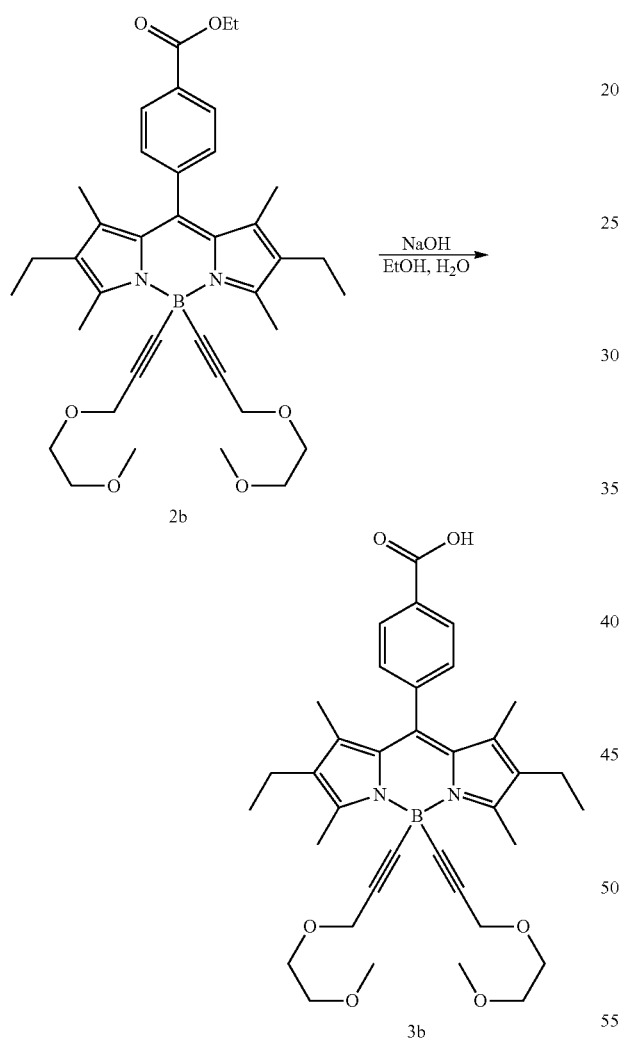

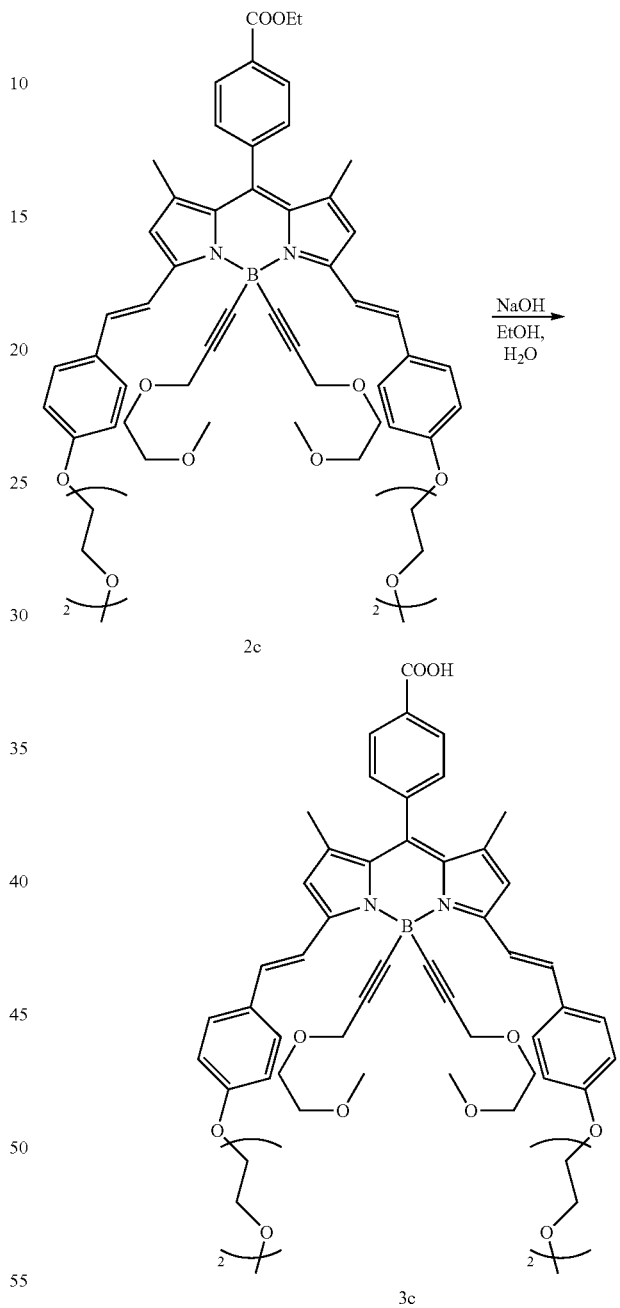

To a solution of compound 2b (840 mg, 1.31 mmol) in 50 mL of ethanol were added 2.10 g of caustic soda (0.525 mol). The solution was stirred for one night at ambient temperature. 30-40 mL of ethyl acetate were added. The organic phase is extracted with water (3×20 mL). The aqueous phases were combined and acidified to pH 1-2 with 1M HCl solution. The aqueous phase was extracted with dichloro-methane. The organic phase was dried over hydrophilic cotton then evaporated to dryness to give the compound 3b in the form of an orange powder (778 mg, 97%).

To a solution of compound 2c (80 mg, 0.080 mmol) in 20 mL of ethanol were added 130 mg of caustic soda (3.22 mmol). The solution was stirred for one night at ambient temperature. 10-20 mL of ethyl acetate were added. The organic phase is extracted with water (3×10 mL). The aqueous phases were combined and acidified to pH 1-2 with 1M HCl solution. The aqueous phase was extracted with dichloro-methane. The organic phase was dried over hydrophilic cotton then evaporated to dryness to give the compound 3c in the form of a blue powder (70 mg, 90%).

Characterization of the Compound 3c $^1$H NMR (CDCl$_3$ 300 MHz): 1.41 (s, 6H), 3.15 (m, 4H), 3.20 (s, 6H), 3.41 (s, 6H), 3.52 (m, 4H), 3.60 (m, 4H), 3.74 (m, 4H), 3.90 (m, 4H), 4.17 (s, 4H), 4.22 (m, 4H), 6.63 (s, 2H), 7.28 (AB sys, 8H, J$_{AB}$=8.6 Hz, ν$_0$δ=120.59 Hz), 7.61 (AB sys, 4H, J$_{AB}$=16.12 Hz, ν$_0$δ=191.44 Hz) 7.88 (AB sys, 4H, J$_{AB}$=8.19 Hz, ν$_0$δ=144.73 Hz).

UV-Vis (CH$_2$Cl$_2$) λ nm (ε, M$^{-1}$ cm$^{-1}$)=647 (118,000), 373 (67,800).

Preparation of the Compound 3d

The compound 3d is prepared according to the following reaction scheme:

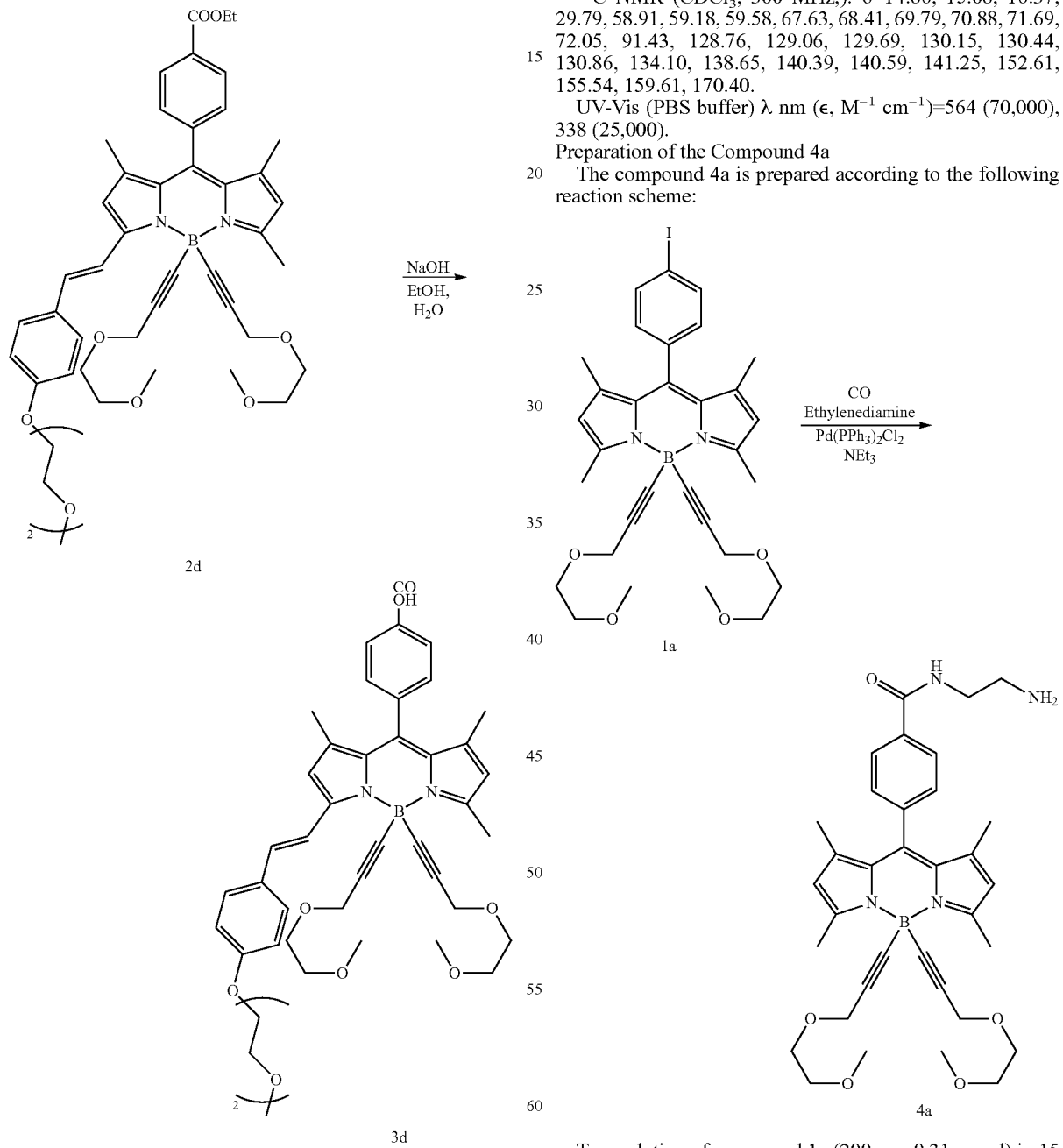

combined and acidified to pH 1-2 with 1M HCl solution. The aqueous phase was extracted with dichloro-methane. The organic phase was dried over hydrophilic cotton then evaporated to dryness to give the compound 3d in the form of an orange powder (70 mg, 90%).

Characterization of the Compound 3d $^1$H NMR (CDCl$_3$ 300 MHz): 1.36 (s, 3H), 1.39 (s, 3H), 2.74 (s, 3H), 3.26 (s, 6H), 3.32 (m, 4H), 3.40 (s, 3H), 3.56 (m, 6H), 3.73 (m, 2H), 3.88 (m, 2H), 4.18 (m, 6H), 6.03 (s, 1H), 6.59 (s, 1H), 7.22 (AB sys, 4H, J$_{AB}$=8.67 Hz, ν$_0$δ=180.18 Hz); 7.58 (AB sys, 2H, J$_{AB}$=16.29 Hz, ν$_0$δ=297.72 Hz), 7.85 (AB sys, 4H, J$_{AB}$=7.99 Hz, ν$_0$δ=226.28 Hz).

$^{13}$C NMR (CDCl$_3$, 300 MHz,): δ=14.86, 15.08, 16.37, 29.79, 58.91, 59.18, 59.58, 67.63, 68.41, 69.79, 70.88, 71.69, 72.05, 91.43, 128.76, 129.06, 129.69, 130.15, 130.44, 130.86, 134.10, 138.65, 140.39, 140.59, 141.25, 152.61, 155.54, 159.61, 170.40.

UV-Vis (PBS buffer) λ nm (ε, M$^{-1}$ cm$^{-1}$)=564 (70,000), 338 (25,000).

Preparation of the Compound 4a

The compound 4a is prepared according to the following reaction scheme:

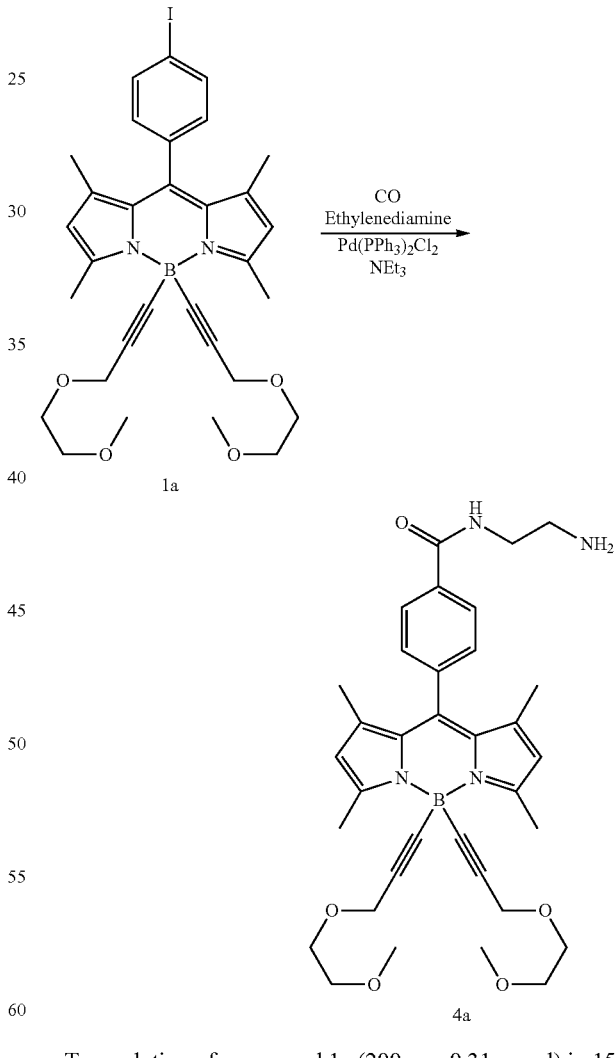

To a solution of compound 2d (80 mg, 0.10 mmol) in 20 mL of ethanol were added 162 mg of caustic soda (4.05 mmol). The solution was stirred for one night at ambient temperature. 10-20 mL of ethyl acetate were added. The organic phase is extracted with water (3×10 mL). The aqueous phases were To a solution of compound 1a (200 mg, 0.31 mmol) in 15 mL of benzene were added 1 mL of ethylenediamine (15 mmol), 66 mg of palladium bis-triphenylphosphine dichloride (0.09 mmol) and 1 mL of triethylamine. The solution was stirred at 70° C. for one night by "bubbling in" carbon monoxide. The reaction mixture was extracted with dichloromethane and washed with water (3×20 mL). The organic phase was dried over hydrophilic cotton and evaporated. The residue was purified by chromatography on a silica column (gradient from $CH_2Cl_2$ 100% to $CH_2Cl_2$ 75:25) to give the compound 4a in the form of an orange powder (160 mg, 80%).

Characterization of the Compound 4a $^1$H NMR ($CDCl_3$, 300 MHz): δ=1.34 (s, 6H), 2.72 (s, 6H), 3.01 (t, 2H, $^3J$=5.7 Hz), 3.36 (s, 6H), 3.55 (m, 6H), 3.64 (m, 4H), 4.20 (s, 4H), 6.01 (s, 2H), 6.98 (t, 1H, $^3J$=5.5 Hz), 7.69 (AB sys, 4H, $J_{AB}$=8.3 Hz, $\nu_0\delta$=162.7 Hz);

$^1$H NMR ($CDCl_3$, 75.4 MHz,): δ=15.0, 16.2, 41.3, 42.2, 59.1, 59.8, 68.7, 71.9, 90.6, 121.9, 127.9, 128.8, 129.4, 134.9, 139.1, 140.4, 141.0, 155.7, 167.0;

$^{11}$B NMR ($CDCl_3$, 128.4 MHz): δ=−10.3 (s);

UV-Vis ($CH_2Cl_2$) λ nm (ε, $M^{-1}$ $cm^{-1}$)=500 (64,500), 371 (5600)

$FAB^+$ m/z: 599.2 ($[M+H]^+$, 100);

Elemental analysis calculated for $C_{34}H_{43}BN_4O_5$: C, 68.23; H, 7.24; N, 9.36. Found: C, 67.84; H, 7.07; N, 9.22.

Preparation of the Compound 5a

The compound 5a is prepared according to the following reaction scheme:

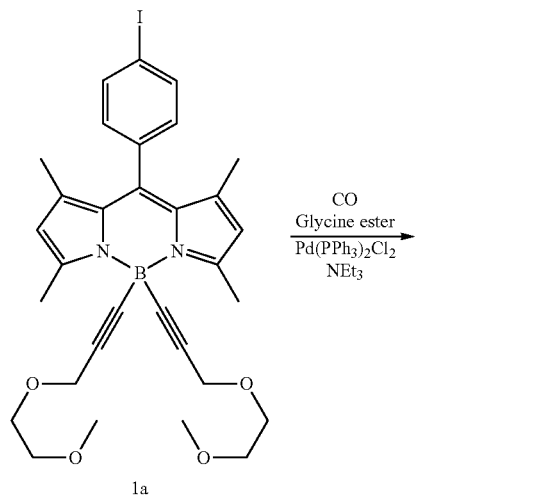

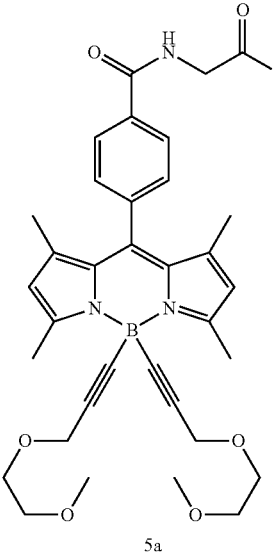

To a solution of compound 1a (100 mg, 0.16 mmol) in 6 mL of anhydrous toluene were added 80 mg of glycine ethyl ester (0.47 mmol), 22 mg of palladium bis-triphenylphosphine dichloride (0.03 mmol) and 2 mL of triethylamine. The solution was stirred at 80° C. for 6 hrs by "bubbling in" carbon monoxide. The reaction mixture was filtered on Celite and partially evaporated. The residue was extracted with dichloromethane and washed with water (2×20 mL). The organic phase was dried over hydrophilic cotton and evaporated. The residue was purified by chromatography on a silica gel column (AcOEt/petroleum ether 50:50) to give the compound 5a in the form of an orange powder (43 mg, 43%).

Characterization of the Compound 5a $^1$H NMR ($CDCl_3$, 300 MHz): δ=1.33 (t, 3H, $^3J$=7.2 Hz), 1.34 (s, 6H), 2.72 (s, 6H), 3.36 (s, 6H), 3.55 (m, 4H), 3.66 (m, 4H), 4.20 (s, 4H), 4.27 (d, 2H, $^3J$=4.5 Hz), 4.29 (q, 2H, $^3J$=7.1 Hz), 6.01 (s, 2H), 6.77 (t, 1H, $^3J$=4.9 Hz), 7.69 (AB sys, 4H, $J_{AB}$=8.3 Hz, $\nu_0\delta$=156.4 Hz);

$^{13}$C {$^1$H} NMR ($CDCl_3$, 75.4 MHz,): δ=14.3, 14.9, 16.2, 42.1, 59.1, 59.8, 61.9, 68.7, 71.9, 91.0, 121.9, 127.9, 129.0, 129.3, 134.2, 139.5, 140.2, 141.0, 155.8, 166.7, 170.2;

$^{11}$B NMR ($CDCl_3$, 128.4 MHz): δ=−10.3 (s);

UV-Vis ($CH_2Cl_2$) λ nm (ε, $M^{-1}$ $cm^{-1}$)=501 (84,200), 366 (4200), 309 (6500).

Preparation of the Compound 6a

The compound 6a is prepared according to the following reaction scheme:

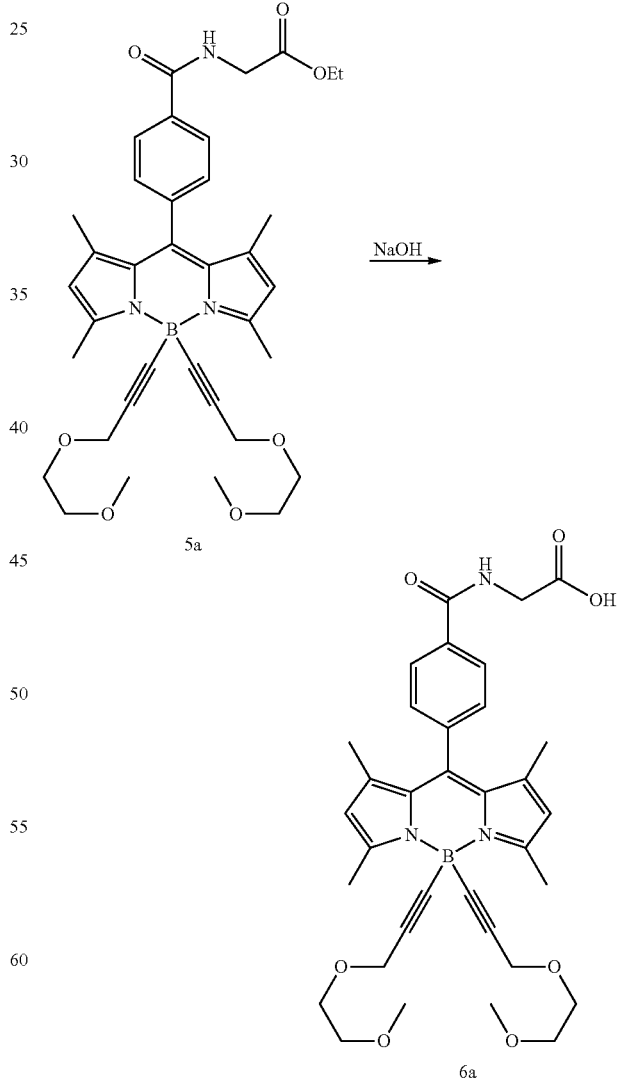

To a solution of compound 5a (40 mg, 0.06 mmol) in ethanol (10 mL) was added an aqueous solution of caustic soda (60 mg, 1.2 mmol). The solution was stirred for 2 hrs at ambient temperature. 10-20 mL of ethyl acetate were added. The organic phase is extracted with water (2×20 mL). The aqueous phases were combined and acidified to pH 1-2 with 1M HCl solution. The product was extracted with dichloromethane. The organic phase was dried over Na2SO4 then evaporated to dryness to give the compound 6a in the form of an orange powder (35 mg, 90%).

Characterization of the Compound 6a $^1$H NMR (CDCl$_3$, 400 MHz): δ=1.32 (s, 6H), 2.72 (s, 6H), 3.36 (s, 6H), 3.55 (m, 4H), 3.66 (m, 4H), 4.19 (s, 4H), 4.27 (d, 2H, $^3$J=3.4 Hz), 4.87 (b, 1H), 6.01 (s, 2H), 7.04 (t, 1H, $^3$J=3.8 Hz), 7.69 (AB sys, 4H, J$_{AB}$=6.0 Hz, ν$_0$5=160.2 Hz);

$^{13}$C NMR (CDCl$_3$, 100 MHz,): S=14.9, 16.2, 42.0, 59.0, 59.7, 68.6, 71.8, 90.9, 121.9, 128.0, 129.0, 129.3, 133.8, 139.6, 140.2, 140.9, 155.8, 167.3, 172.3;

$^{11}$B NMR (CDCl$_3$, 128.4 MHz): δ=−10.2 (s);

UV-Vis (CH$_2$Cl$_2$) λ nm (ε, M$^{-1}$ cm$^{-1}$)=501 (65,000), 366 (3800), 309 (5900);

UV-Vis (PBS buffer) λ nm (ε, M$^{-1}$ cm$^{-1}$)=496 (59,600), 367 (4100), 308 (6100).

Preparation of the Compound 7a

The compound 7a is prepared according to the following reaction scheme:

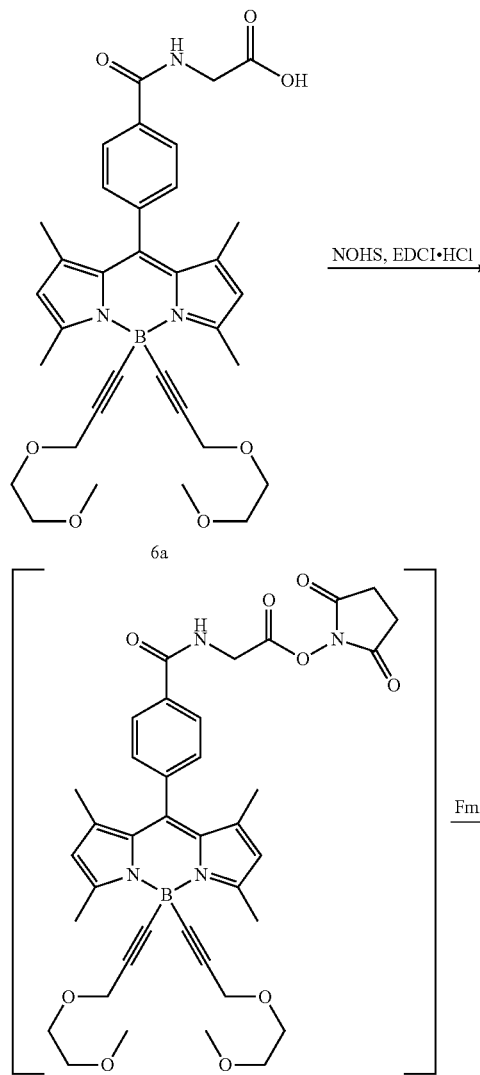

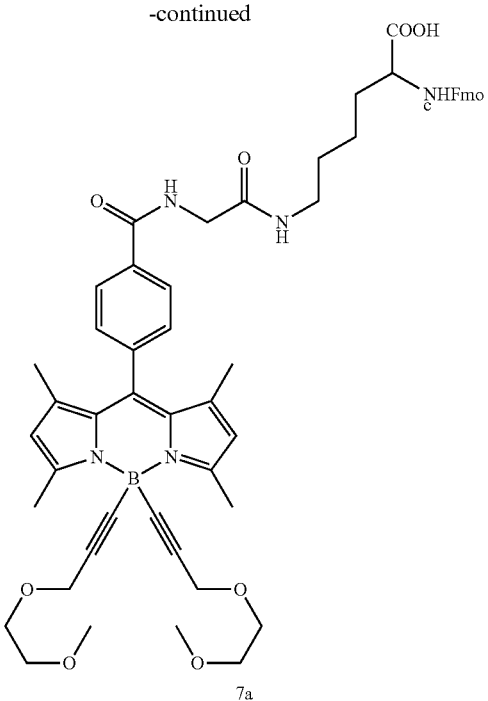

To a solution of compound 6a (25 mg, 0.04 mmol) and N-hydroxysuccinimide (7 mg, 0.06 mmol) in dichloromethane (5 mL) were added, at 0° C., 12 mg of N-dimethyl-3-aminopropyl-carbodiimide (0.06 mmol). The reaction medium was stirred for one night while allowing the bath to return to ambient temperature. The solution was diluted in dichloromethane, washed with a 1M hydrochloric acid solution (2×20 mL), with a 5% NaHCO$_3$ solution, then with a saturated NaCl solution. The organic phase was dried over Na$_2$SO$_4$ then evaporated to dryness under reduced pressure. The residue was dissolved in acetonitrile (5 mL). To this solution was added a solution of Fmoc-Lys-OH (16 mg, 0.04 mmol) and K$_2$CO$_3$ (11 mg, 0.08 mmol) in an acetonitrile/water mixture (5 mL/1 mL). The solution was stirred at ambient temperature for 1 hr, then it was extracted with ethyl acetate. The organic phase was washed with water (2×20 mL), dried over MgSO$_4$ and evaporated. The residue was purified by chromatography on an eluted silica column (gradient from AcOEt 100% to AcOEt/EtOH 90:10). The aqueous phases were combined, acidified with a 1M hydrochloric acid solution to pH 1 and extracted with dichloromethane. The resulting organic phase was dried over MgSO$_4$ and evaporated. The different fractions were combined to give the compound 7a in the form of an orange powder (25 mg, 64%).

Characterization of the Compound 7a $^1$H NMR (CDCl$_3$, 300 MHz): δ=1.27 (s, 6H), 1.35-1.82 (m, 6H), 2.67 (s, 6H), 3.21-3.31 (m, 8H), 3.49 (m, 4H), 3.61 (m, 4H), 3.99-4.36 (m, 10H), 5.95 (s, 2H), 7.22-7.39 (m, 6H), 7.54-7.58 (m, 2H), 7.70 (d, 2H, $^3$J=7.5 Hz), 7.93 (d, 2H, $^3$J=7.7 Hz);

$^{13}$C {$^1$H} NMR (CDCl$_3$, 75.4 MHz,): δ=14.7, 16.0, 23.4, 28.6, 31.5, 31.9, 39.1, 43.3, 53.6, 58.9, 59.6, 67.0, 68.5, 71.7, 90.7, 118.8, 120.0, 121.8, 123.3, 125.1, 127.1, 127.8, 128.0, 129.2, 129.8, 133.9, 139.4, 140.2, 140.9, 141.3, 143.8, 143.9, 155.6, 156.4, 167.5, 169.2;

ESI m/z: 986.4 ([M+Na]$^+$, 100).

Preparation of the Compound 5a[13]

The compound 5a[13] is prepared according to the following reaction scheme:

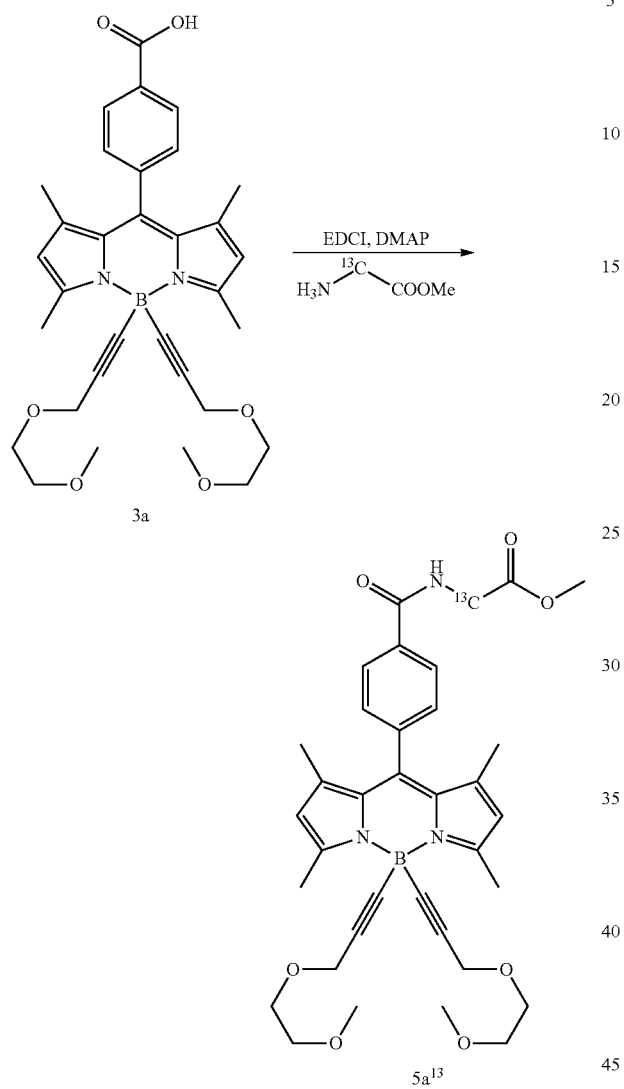

To a solution of compound 3a (570 mg, 1.025 mmol) in dichloromethane (30 mL) were added, at 0° C., 294 mg of N-dimethyl-3-aminopropylcarbodiimide (1.537 mmol) and 187 mg of dimethylaminopyridine (1.537 mmol). The reaction medium was stirred for one hour at ambient temperature. To this solution were then added 142 mg of carbon 13 labeled glycine ester (1.127 mmol). The reaction medium was stirred for one hour at ambient temperature. The solution was diluted in dichloromethane, washed with water (2×20 mL), with a 5% NaHCO$_3$ solution, then with a saturated NaCl solution. The organic phase was dried over Na$_2$SO$_4$ then evaporated to dryness under reduced pressure. The residue was purified by chromatography on a silica column eluted with an ethyl acetate/petroleum ether gradient 20/80, 30/70, 40/60, to give the compound 5a[13] in the form of an orange powder (527 mg, 82%).

Characterization of the Compound 5a[13]

$^1$H NMR (CDCl$_3$ 300 MHz): 1.32 (s, 6H), 2.71 (s, 6H), 3.34 (s, 6H), 3.52 (m, 4H), 3.64 (m, 4H), 4.02 (d, 1H, $^1$J=141.3 Hz, $^3$J=4.4 Hz), 4.18 (s, 4H), 4.50 (d, 1H, J=141.3 Hz, $^3$J=4.4 Hz), 6.00 (s, 2H), 6.85 (s, 1H), 7.68 (AB sys, 4H, J$_{AB}$=8 Hz, ν$_0$δ=159.56 Hz).

$^{13}$C NMR (CDCl$_3$, 300 MHz,): δ=14.72, 16, 41.72, 52.48, 58.86, 59.54, 68.44, 71.66, 76.57, 77, 77.42, 121.66, 127.78, 128.71, 129.06, 133.88, 139.24, 140, 140.72, 155.51, 166.58, 169.976, 170.79.

Preparation of the Compound 6a[13]

The compound 6a[13] is prepared according to the following reaction scheme:

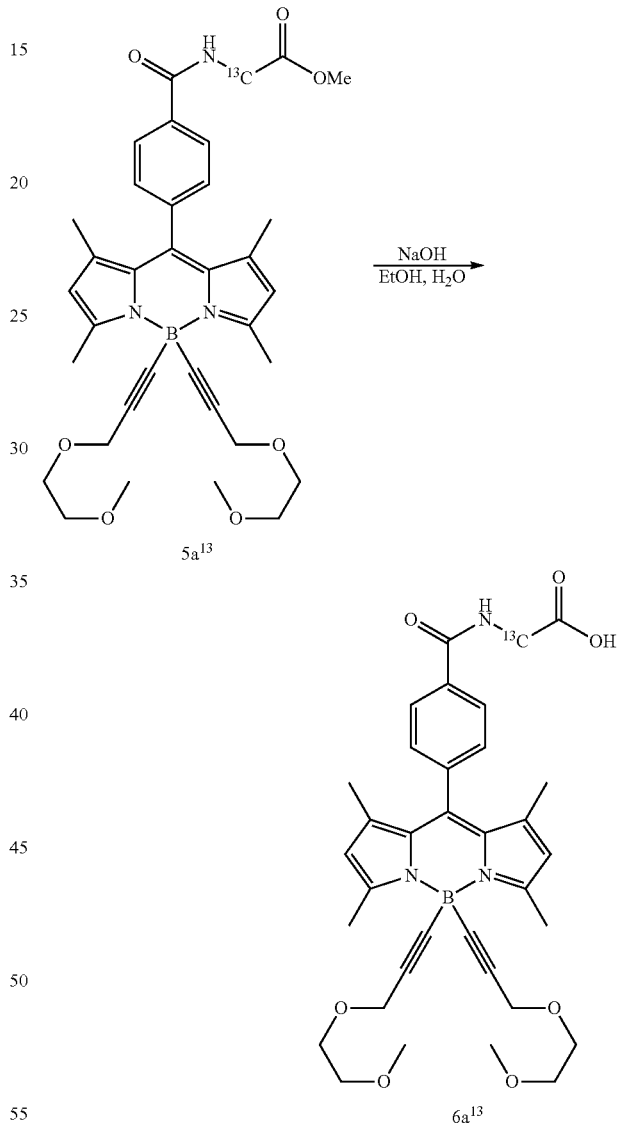

To a solution of compound 5a[13] (500 mg, 0.795 mmol) in ethanol (30 mL) was added an aqueous solution of caustic soda (1.27 g, 32 mmol). The solution was stirred for 2 hrs at ambient temperature. 20-30 mL of ethyl acetate were added. The organic phase is extracted with water (3×20 mL). The aqueous phases were combined and acidified to pH 1-2 with 1M HCl solution. The aqueous phase was extracted with dichloromethane. The organic phase was dried over hydrophilic cotton then evaporated to dryness to give the compound 6a[13] in the form of an orange powder (464 mg, 95%).

Characterization of the Compound 6a[13]

$^1$H NMR (CDCl$_3$ 300 MHz): δ=1.29 (s, 6H), 2.70 (s, 6H), 3.34 (s, 6H), 3.52 (m, 4H), 3.65 (m, 4H), 3.93 (s, 1H, [1]J=140.6 Hz), 4.17 (s, 4H), 4.39 (s, 1H, [1]J=140.6 Hz), 7.67 (AB sys, H, J$_{AB}$=7.72 Hz, ν$_0$δ=177.95 Hz).

$^{13}$C NMR (CDCl$_3$, 300 MHz,): δ=14.72, 15.43, 16.03, 42.20, 43.02, 54.94, 58.36, 58.85, 59.55, 68.46, 71.63, 76.57, 90.76, 121.74, 127.94, 128.74, 129.05, 133.70, 139.35, 139.94, 140.68, 140.78, 155.26, 155.48, 155.57, 167.35.

Preparation of the Compound 7a[13]

The compound 7a[13] is prepared according to the following reaction scheme:

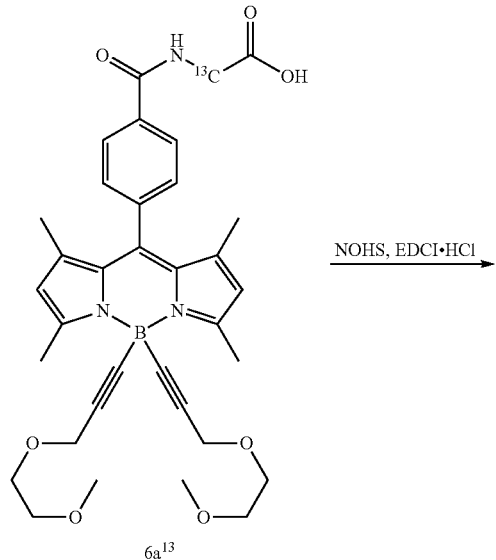

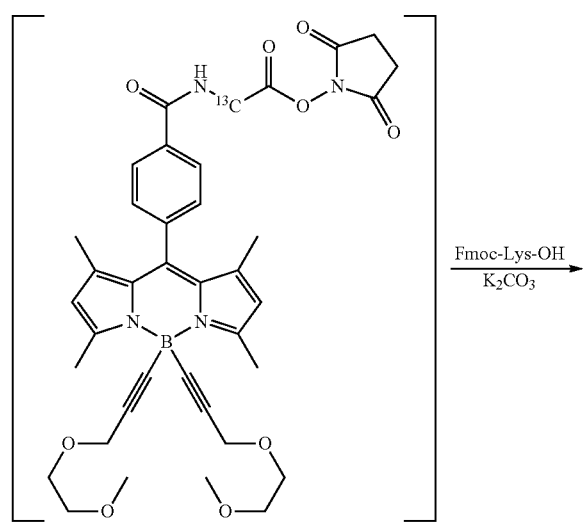

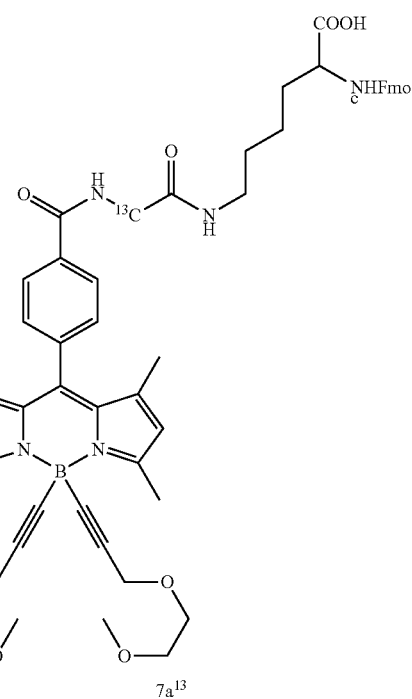

To a solution of compound 6a[13] (430 mg, 0.7 mmol) and N-hydroxysuccinimide (120 mg, 1.05 mmol) in dichloromethane (50 mL) were added, at 0° C., 207 mg of N-dimethyl-3-aminopropylcarbodiimide (1.05 mmol). The reaction medium was stirred for one night while allowing the bath to return to ambient temperature. The solution was diluted in dichloromethane, washed with a 1M hydrochloric acid solution (3×20 mL), with a 5% NaHCO$_3$ solution, then with a saturated NaCl solution. The organic phase was dried over Na$_2$SO$_4$ then evaporated to dryness under reduced pressure. The residue was dissolved in acetonitrile (50 mL). To this solution was added a solution of Fmoc-Lys-OH (566 mg, 1.40 mmol) and K$_2$CO$_3$ (193 mg, 1.40 mmol) in an acetonitrile/water mixture (15 mL/5 mL). The solution was stirred at ambient temperature for 2 hrs, then it was extracted with ethyl acetate. The organic phase was washed with water (3×20 mL), dried over MgSO$_4$ and evaporated. The residue was purified by chromatography on a silica column eluted with a gradient ranging from AcOEt 100% to AcOEt/EtOH 90:10. The different fractions were combined to give the compound 7a[13] in the form of an orange powder (539 mg, 80%).

Characterization of the Compound 7a[13]

$^1$H NMR (MeOD 400 MHz 60° C.): δ=1.18 (m, 1H), 1.22 (s, 6H), 1.40 (m, 2H), 1.53 (m, 2H), 2.71 (s, 6H), 3.23 (t, 2H, [3]J=6.72 Hz) 3.34 (s, 6H), 3.51 (m, 4H), 3.63 (m, 4H), 4.14 (s, 4H), 4.18 (t, 1H, [3]J=5.10 Hz), 4.21 (d, 2H, [1]JHC[13]=140 Hz), 6.04 (s, 2H), 7.25 (m, 2H), 7.33 (m, 4H), 7.61 (m, 2H), 7.71 (d, 2H), 8.01 (d, 2H).

Preparation of the Compound 5b

The compound 5b is prepared according to the following reaction scheme:

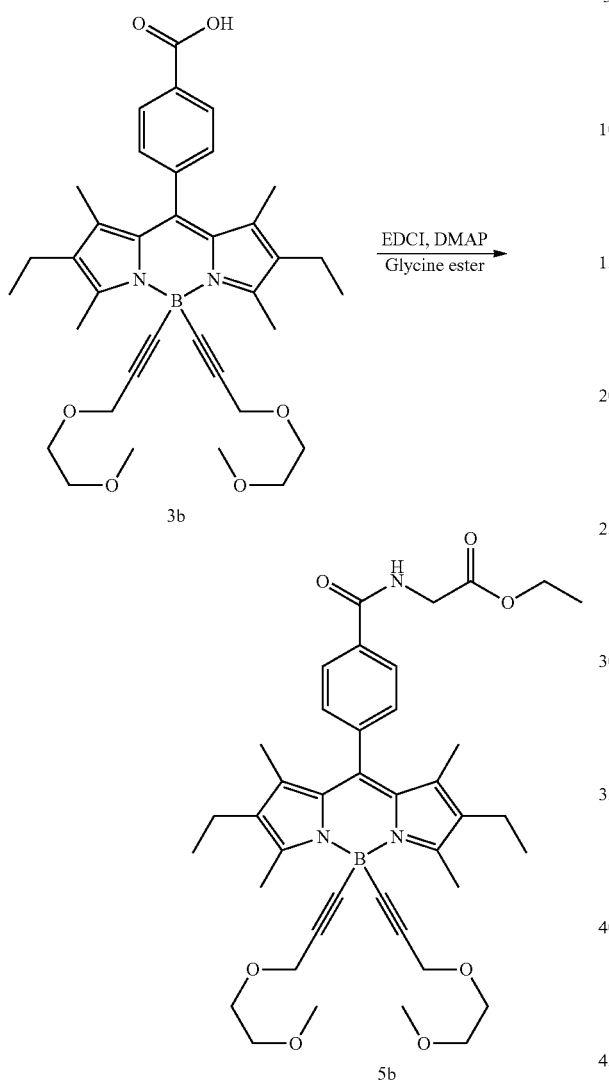

To a solution of compound 3b (600 mg, 0.979 mmol) in dichloromethane (50 mL) were added, at 0° C., 280 mg of N-dimethyl-3-aminopropylcarbodiimide (1.47 mmol) and 180 mg of dimethylaminopyridine (1.47 mmol). The reaction medium was stirred for one hour at ambient temperature. To this solution was then added 205 mg of glycine ester (1.47 mmol). The reaction medium was stirred for one hour at ambient temperature. The solution was diluted in dichloromethane, washed with water (2×20 mL), with a 5% NaHCO$_3$ solution then with a saturated NaCl solution. The organic phase was dried over Na$_2$SO$_4$ then evaporated to dryness under reduced pressure. The residue was purified by chromatography on a silica column eluted with an ethyl acetate/petroleum ether 20/80, 30/70, 40/60 gradient, to give the compound 5b in the form of an orange powder (560 mg, 82%).

Characterization of the Compound 5b $^1$H NMR (CDCl$_3$ 300 MHz): 0.97 (t, 6H, $^3$J=7.35 Hz), 1.22 (s, 6H) 1.31 (t, 2H, $^3$J=7.10 Hz), 2.28 (q, 4H, $^3$J=7.5 Hz) 2.68 (s, 6H), 3.34 (s, 6H), 3.53 (m, 4H), 3.64 (m, 4H), 4.18 (s, 4H), 4.25 (m, 4H), 6.84 (t, 1H, $^3$J=4.7 Hz), 7.78 (AB sys, 4H, J$_{AB}$=8.5 Hz, ν$_0$δ=300.4 Hz);

$^{13}$C NMR (CDCl$_3$, 300 MHz,): δ=12.08, 14.05, 14.25, 14.75, 15.34, 17.38, 29.72, 42.05, 59, 59.76, 61.85, 68.55, 71.83, 90.62, 127.81, 128.66, 129.16, 133.11, 133.91, 136.02, 138.60, 140.27, 154.04, 166.80, 170.14.

Preparation of the Compound 6b

The compound 6b is prepared according to the following reaction scheme:

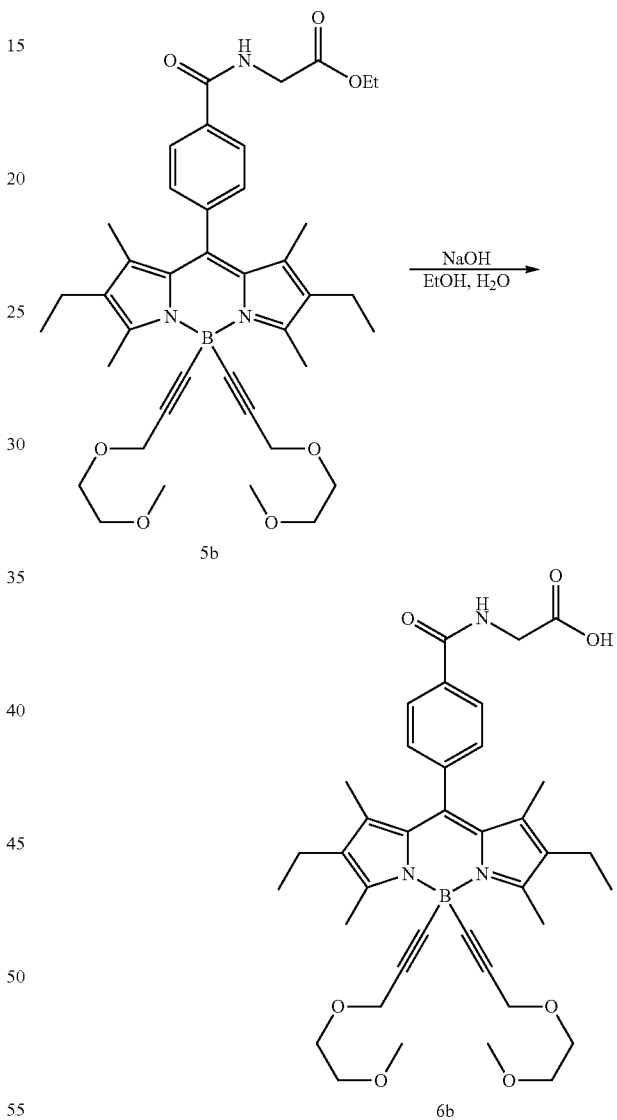

To a solution of compound 5b (510 mg, 0.732 mmol) in ethanol (50 mL) was added an aqueous solution of caustic soda (1.20 g, 30 mmol). The solution was stirred for 2 hrs at ambient temperature. 20-30 mL of ethyl acetate were added. The organic phase is extracted with water (3×20 mL). The aqueous phases were combined and acidified to pH 1-2 with 1M HCl solution. The aqueous phase was extracted with dichloromethane. The organic phase was dried over hydrophilic cotton then evaporated to dryness to give the compound 6b in the form of an orange powder (490 mg, quantitative).

Characterization of the Compound 6b $^1$H NMR (CDCl$_3$ 300 MHz): δ=0.96 (t, 6H, $^3$J=7.3 Hz), 1.22 (s, 6H), 2.30 (q, 4H, $^3$J=7.3 Hz), 2.68 (s, 6H), 3.34 (s, 6H), 4.19 (s, 4H), 3.54 (m, 4H), 3.66 (m, 4H), 4.18 (s, 4H), 4.26 (d, 2H, $^3$J=4.8 Hz), 7.13 (t, 1H, $^3$J=4.8 Hz), 7.40 (AB sys, H, J$_{AB}$=6.0 Hz, ν$_0$δ=160.2 Hz);

$^{13}$C NMR (CDCl$_3$, 300 MHz,): δ=12.08, 14.03, 14.73, 17.35, 41.93, 58.91, 59.71, 68.48, 71.74, 90.51, 127.90, 128.60, 129.18, 133.14, 133.57, 136.01, 138.54, 140.39, 154.04, 167.35, 172.29.

Preparation of the Compound 7b

The compound 7b is prepared according to the following reaction scheme:

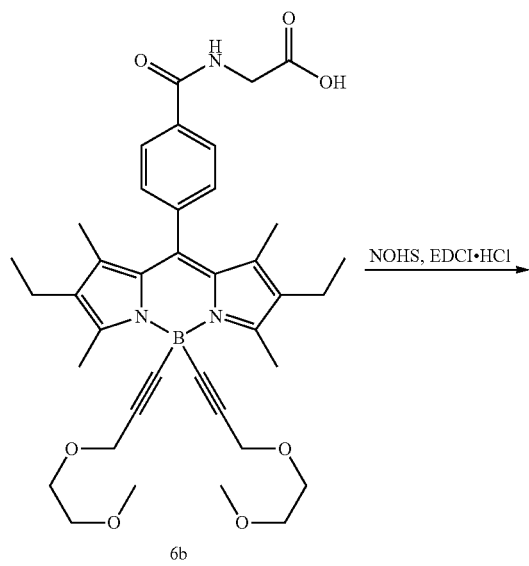

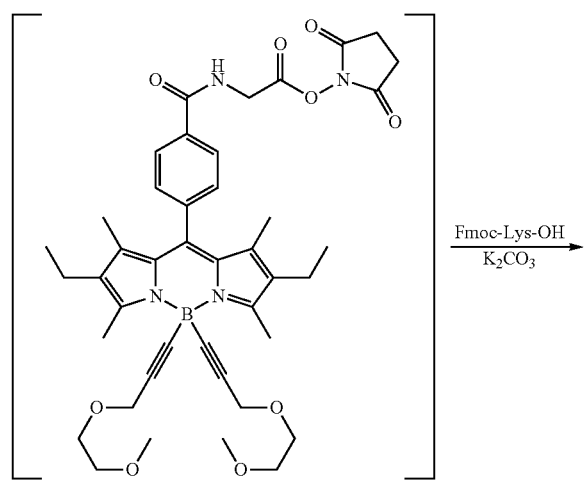

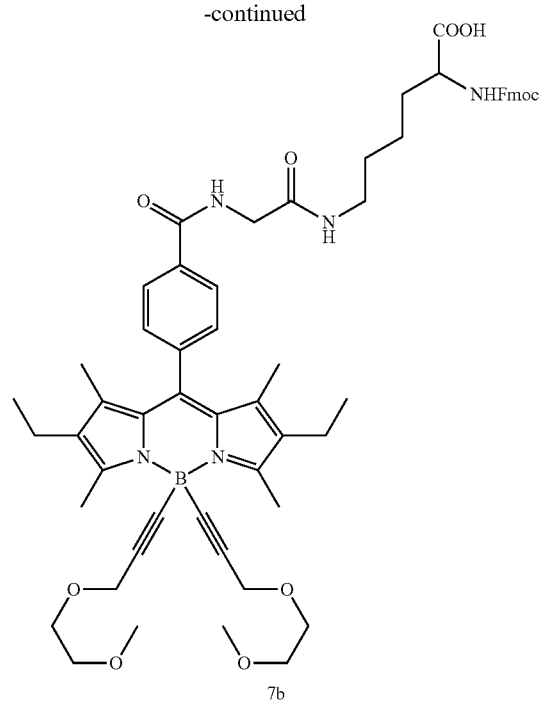

To a solution of compound 6b (430 mg, 0.643 mmol) and N-hydroxysuccinimide (112 mg, 0.968 mmol) in dichloromethane (50 mL) were added, at 0° C., 190 mg of N-dimethyl-3-aminopropylcarbodiimide (0.968 mmol). The reaction medium was stirred for one night while allowing the bath to return to ambient temperature. The solution was diluted in dichloromethane, washed with a 1M hydrochloric acid solution (3×20 mL), with a 5% NaHCO$_3$ solution then with a saturated NaCl solution. The organic phase was dried over Na$_2$SO$_4$ then evaporated to dryness under reduced pressure. The residue was dissolved in acetonitrile (50 mL). To this solution was added a solution of Fmoc-Lys-OH (522 mg, 1.29 mmol) and K$_2$CO$_3$ (180 mg, 1.29 mmol) in an acetonitrile/water mixture (15 mL/5 mL). The solution was stirred at ambient temperature for 2 hrs, then it was extracted with ethyl acetate. The organic phase was washed with water (3×20 mL), dried over MgSO$_4$ and evaporated. The residue was purified by chromatography on a silica column eluted with a gradient from AcOEt 100% to AcOEt/EtOH 90:10. The different fractions were combined to give the compound 7b in the form of an orange powder (491 mg, 75%).

Characterization of the Compound 7b $^1$H NMR (MeOD 400 MHz 60° C.): δ=0.98 (t, 6H, $^3$J=7.50 Hz), 1.26 (s, 6H), 1.41 (m, 2H), 1.55 (m, 2H), 2.33 (q, 4H, $^3$J=7.50 Hz), 2.71 (s, 6H), 3.24 (t, 2H, $^3$J=5.10 Hz) 3.34 (s, 6H), 3.51 (m, 4H), 3.63 (m, 4H), 4.06 (s, 3H), 4.14 (s, 4H), 4.19 (t, 1H, $^3$J=5.10 Hz), 4.37 (m, 2H), 7.30 (m, 6H), 7.62 (m, 2H), 7.87 (AB sys, H, J$_{AB}$=7.66 Hz, ν$_0$δ=112.84 Hz).

EXAMPLE 2

Synthesis of a Peptide Containing a Lysine Labeled with a Compound of General Formula (I) According to the Invention The compound 7a (labeled lysine) prepared according to example 1 is used in an automatic peptide synthesizer and substituted for the lysine in position 16 of the following amino acid sequence corresponding to human beta-amyloid peptide 1-42: H-Asp-Ala-Glu-Phe-Arg-His-Asp-Ser-Gly-Tyr-Glu-Val—His-His-Gln-Lys*-Leu—Val-Phe-Phe-Ala-Glu-Asp-Val-Gly-Ser-Asn—Lys-Gly-Ala-Ile—Ile-Gly-Leu-Met-Val-Gly-Gly-Val—Val-Ile-Ala-OH (SEQ ID No.: 1).

The peptide is utilized in examples 3, 4 and 5 and is hereinafter referred to as labeled amyloid peptide.

Protocol Common to Examples 3 and 4

PC12 cells (derived from male rat medullo-adrenal gland tumor) are inoculated into glass-bottomed Petri dishes previously treated with collagen and polyornithine. They are cultured for 7 days in an atmosphere containing 5% of $CO_2$ at 37° C. in RPMI 1640 medium containing glutamine and supplemented with 10% of horse serum, 5% of fetal calf serum, 50 U/mL of penicillin and 50 µg/mL of streptomycin. To induce the differentiation of the cells, 50 ng/mL of murine neurotrophic growth factor (NGF) 2.5S are added to the medium 24 hours after the inoculation.

The day before the measurement, unlabeled beta-amyloid peptide 1-42 of SEQ. ID. No.: 1 or the corresponding unlabeled reverse peptide (42-1) of SEQ ID No.: 2 is added at different concentrations lying between 10 and 1000 nmol·$L^{-1}$.

The following day, this preparation is washed 3 times with Krebs medium at ambient temperature and placed on an inverted microscope coupled with a spectro-fluorimeter. A fluorescence spectrum (excitation 480 nm; emission 495-600 nm) of the base line is recorded before the addition of the labeled amyloid peptide (250 nmol·$L^{-1}$). A second fluorescence spectrum is recorded after 10 minutes of incubation.

EXAMPLE 3

Measurement of the Value of the Spectral Index of the Compound 7a Coupled to the Beta-Amyloid Peptide 1-42 after Preincubation with the Unlabeled Beta-Amyloid Peptide The base line spectrum is subtracted from the fluorescence spectrum of the labeled amyloid peptide. The spectrum obtained is broken down into 4 component Gaussian curves by deconvolution and non-linear regression as illustrated in FIG. 4, this fluorescence spectrum (black line) can be broken down into component Gaussian curves (lines in different shades of gray) by means of spectrum deconvolution software (Peakfit, Seasolve Software Inc., www.seasolve.com) (Graph A). The ratio of the amplitude (measured graphically or else with the deconvolution software) of the Gaussian curves centered respectively at 525 nm and 540 nm defines a spectral index describing the distribution of the spectrum Graph B shows the deconvolution of the fluorescence spectrum of the labeled amyloid peptide recorded in the presence of PC12 cells before preincubation (solid lines) and after preincubation (dotted lines) of the cells in the presence of unlabeled beta-amyloid peptide 1-42. A considerable increase in the amplitude of the Gaussian curve centered at 525 nm which results in an increase in the spectral index is observed when the cells were placed beforehand in the presence of unlabeled beta-amyloid peptide 1-42.

Thus it is observed that the preincubation of the cells with the unlabeled beta-amyloid peptide 1-42 leads to a change in the spectrum and the presence of the beta-amyloid peptide 1-42 can be detected in a sample.

EXAMPLE 4

Measurement of the Value of the Spectral Index of the Compound 7a Coupled to the Beta-Amyloid Peptide 1-42 after Preincubation with Different Concentrations of Unlabeled Beta-Amyloid Peptide According to the same experimental principle, the value of the spectral index of the compound 7a coupled to the beta-amyloid peptide 1-42 is measured after preincubation at different concentrations of unlabeled beta-amyloid peptide of SEQ ID No.: 1.

The PC12 cells are preincubated for 12 hours in the presence of unlabeled beta-amyloid peptide 1-42 or 42-1 then rinsed before being placed under a microscope coupled to a spectrofluorimeter. A first spectrum (base line) is recorded.

Next, the labeled beta-amyloid peptide is added. A spectrum is recorded 10 minutes after the addition of the fluorescent compound.

The spectral index is the ratio between the amplitude of the first and that of the second Gaussian calculated by deconvolution (see FIG. 4).

The results are shown in FIG. 5:
in the absence of unlabeled beta-amyloid peptide 1-42 (first histogram),
in the presence of 100 nM of unlabeled beta-amyloid peptide 1-42 (second histogram),
in the presence of 250 nM of unlabeled beta-amyloid peptide 1-42 (third histogram),
in the presence of 250 nM of unlabeled beta-amyloid peptide 42-1 (fourth histogram).

The value of the spectral index of fluorescence of the probe varies as a function of the concentration of unlabeled beta-amyloid peptide 1-42 present during the cell preincubation phase. An absence of change in the value of the spectral index is also observed when the cells are incubated in the presence of inactive β-amyloid peptide 42-1. (Student t-test: *** $p<0.5\%$ as regards Ab 0 nM; °° $p<1\%$ as regards Ab 1-42 250 nM). This graph represents 4 independent experiments measured in triplicate.

FIG. 5 shows that the change in the value of the ratio is specifically induced by the beta-amyloid peptide 1-42 and that this value increases with the increase in concentration of peptide preincubated; in addition, it is seen that the beta-amyloid peptide 42-1 has no significant effect on the value of the ratio.

Thus, the analysis of the fluorescence spectrum of the probe makes it possible to evaluate the concentration of beta-amyloid peptide at which the cells were preincubated.

EXAMPLE 5

Change in the Value of the Spectral Index of Beta-Amyloid Peptide 1-42 Coupled to the Compound 7a in the Presence of Rat Erythrocytes Preincubated with the Unlabeled Beta-Amyloid Peptide 1-42

A sample of rat blood (1 to 3 ml) is collected in a heparinized tube. The sample is diluted with Krebs medium then centrifuged three times discarding the buffer layer ("buffy coat"). The erythrocytes obtained are next incubated at 37° C. for 2 hours in the presence of the unlabeled beta-amyloid peptide 1-42 or the corresponding unlabeled reverse peptide (42-1) at various concentrations (10-1000 nmol·$L^{-1}$). After an additional washing, the cells are placed in a spectro-fluorimeter and a fluorescence spectrum (excitation 480 nm; emission 495-600 nm) of the base line is recorded before the addition of the labeled amyloid peptide (250 nmol·L$^{-1}$). A second fluorescence spectrum is recorded after 10 minutes of incubation in the presence of the labeled amyloid peptide.

The base line spectrum is subtracted from the fluorescence spectrum of the labeled beta-amyloid peptide. The spectrum obtained is broken down into 4 component Gaussian curves by deconvolution and non-linear regression. The ratio of the amplitude of the Gaussian centered around 510 nm to the amplitude of the Gaussian centered around 530 nm is calculated. Its value varies as a function of the concentration of unlabeled beta-amyloid peptide 1-42 in the presence of which the cells were incubated as illustrated in FIG. 6.

The histogram of FIG. 6 shows that the value of the spectral index increases as a function of the concentration of unlabeled beta-amyloid peptide utilized during the preincubation of the cells.

The invention claimed is:

1. A process for preparing a compound of general formula (I)

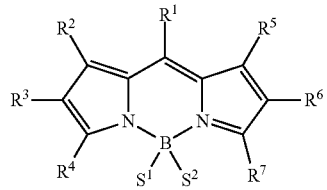

(I)

wherein:

—$R^1$ is selected from the group consisting of —Ar—CO—Z, a hydrogen atom (—H), -LH, -G and -L-G;

—$R^3$, —$R^4$, —$R^6$ and —$R^7$ are each independently selected from the group consisting of —(Ar)$_m$—CO—Z, a hydrogen atom (—H), -L-H, -G and -L-G, wherein exactly one of the substituents $R^1$, $R^3$, $R^4$, $R^6$ and $R^7$ is —Ar—CO—Z or —(Ar)$_m$—CO—Z, respectively;

—m is 0 or 1;

—$R^2$ and —$R^5$ are each independently selected from the group consisting of a hydrogen atom (—H), -L-H, -G and -L-G;

—$S^1$ and —$S^2$ are each independently selected hydrophilic groups of formula —C≡C-L'-A;

—Ar is a $C_5$-$C_{14}$ arylene or heteroarylene, substituted by the group —CO—Z;

—Z is selected from the group consisting of —OH, —O-succinimide, —O-maleimide, -N-glycine, —N-lysine, —Y-L"-COOH and —Y-L"-SH where Y is N or O;

—L and -L" are each independently selected from the group consisting of a single bond, an optionally branched $C_1$-$C_{10}$ carbon chain, a $C_6$-$C_{16}$ arylene, a $C_2$-$C_4$ alkynylene, a linear or branched $C_1$-$C_{20}$ carbon chain interrupted by 1 to 10 oxygen atoms, a linear or branched saturated $C_1$-$C_{20}$ carbon chain interrupted by one to four amide functions —CO—NH—, a nucleotide segment and a sugar segment;

—G is selected from the group consisting of succinimidyl ester, sulfa-succinimidyl ester, isothiocyanate, isocyanate, iodoacetamide, maleimide, sulfonyl halides, phosphoramidates, $C_2$-$C_5$ alkylimidates, $C_6$-$C_{10}$ arylimidates, acid halides, hydrazines substituted with a $C_1$-$C_4$ alkyl, hydroxylamines substituted with a $C_1$-$C_4$ alkyl, carbodiimides and perfluoro-phenols;

—L' is selected from the group consisting of a single bond, a $C_1$-$C_{10}$ alkenylene and a linear or branched saturated $C_1$-$C_{20}$ carbon chain interrupted by 1 to 10 oxygen atoms; and —A is selected from the group consisting of $C_1$-$C_4$ alkyl, a phosphate group and a sulfonate group, said process comprising transforming the synthetic intermediate $$P—(Ar)_m\text{-}Q$$

into a compound of general formula (I) by reacting the intermediate with a carbon source in the presence of a nucleophile selected from the group consisting of water, an alcohol, an amine and a thiol, and of a palladium-containing catalyst; wherein P is a structure identical to the compound of general formula (I) with the exception of the radical $R^1$ or $R^3$ or $R^4$ or $R^6$ or $R^7$ depending on which is the group —Ar—CO—Z for $R^1$ or —$(Ar)_m$—CO—Z for $R^3$ or $R^4$ or $R^6$ or $R^7$, said radical being a bond linked to —$(Ar)_m$-Q, Ar is as defined for the general formula (I), m is 0 or 1, with m being 1 when $R^1$ is —Ar—CO—Z and Q is selected from the group consisting of a halogen atom, an —O-triflate, an —O-tosylate and an —O-mesylate.

2. A labeled molecule of general formula (II):

$$P—(Ar)_m—CO—(X)_n\text{-}T \quad (II)$$

wherein:

—P is the compound of general formula (I)

wherein:

—$R^{1\prime}$ is a bond linked to —$(Ar)_m$—CO—$(X)_n$-T;

—$R^2$, —$R^3$, —$R^4$, —$R^5$, —$R^6$ and —$R^7$ are each independently selected from the group consisting of a hydrogen atom (—H), -L-H, -G and -L-G;

—$S^1$ and —$S^2$ are each independently selected hydrophilic groups of formula —C≡C-L'-A;

—Z is selected from the group consisting of —OH, —O-succinimide, —O-maleimide, —N-glycine, —N-lysine, —Y-L"-$NH_2$, —Y-L"-COOH and —Y-L"-SH where Y is N or O;

—L and -L" are each independently selected from the group consisting of a single bond, an optionally branched $C_1$-$C_{10}$ carbon chain, a $C_6$-$C_{16}$ arylene, a $C_2$-$C_4$ alkynylene, a linear or branched $C_1$-$C_{20}$ carbon chain interrupted by 1 to 10 oxygen atoms, a linear or branched saturated $C_1$-$C_{20}$ carbon chain interrupted by one to four amide functions —CO—NH—, a nucleotide segment and a sugar segment;

—G is selected from the group consisting of succinimidyl ester, sulfo-succinimidyl ester, isothiocyanate, isocyanate, iodoacetamide, maleimide, sulfonyl halides, phosphoramidates, $C_2$-$C_5$ alkylimidates, $C_6$-$C_{10}$ arylimidates, acid halides, hydrazines substituted with a $C_1$-$C_4$ alkyl, hydroxylamines substituted with a $C_1$-$C_4$ alkyl, carbodiimides and perfluoro-phenols;

—L' is selected from the group consisting of a linear or branched saturated $C_1$-$C_{20}$ carbon chain interrupted by 1 to 10 oxygen atoms; and —A is a methyl radical, —Ar is a $C_5$-$C_{14}$ arylene or heteroarylene, —m is 0 or 1, with m being 1 when the —$(Ar)_m$—CO—$(X)_n$-T group is substituted at $R^1$, —X is a spacer bearing a carboxyl, amine or thiol function, —n is 0 or 1, and —T is selected from the group consisting of a natural or synthetic amino acid, a polypeptide, biotin, a nucleotide and a nucleic acid.

3. The labeled molecule as claimed in claim 2, wherein T the beta-amyloid peptide 1-42 of SEQ ID NO: 1, one or more amino acids of which have been replaced by the same amino acid labeled with a fluorescent compound of general formula (I), and including one or more insertions of a labeled amino acid in any part of the peptide chain.

4. The labeled molecule as claimed in claim 2, wherein X is a chain containing at least one amino acid or a $C_1$-$C_6$ alkylene which can be interrupted by 2 or 3 oxygen atoms.

5. A process for preparing the labeled molecule as claimed in claim 2 where T is an amino acid, comprising transforming a compound of general formula (I), where Z contains a terminal carboxylic acid into the corresponding hydroxysuccinimide ester and reacting with T.

6. A process for preparing the labeled molecule as claimed in claim 2 where T is biotin, comprising transforming a compound of general formula (I) where Z bears a carboxylic acid into the corresponding amide by reacting the carboxylic acid with an aliphatic diamine followed by reacting with a biotin.

7. A process for preparing the labeled molecule as claimed in claim 2 where T is a nucleotide, comprising reacting a compound of general formula (I) where Z bears a carboxylic acid, with a modified nucleotide containing a free amine function.

8. A diagnostic kit comprising at least one labeled molecule as claimed in claim 2.

9. The process as claimed in claim 1, wherein $R^2$ and $R^5$ are identical, $R^3$ and $R^6$ are identical, $R^4$ and $R^7$ are identical, and $S^1$ and $S^2$ are identical.

10. The process as claimed in claim 1, wherein Ar is selected from the group consisting of benzene, naphthalene, anthracene, pyrene, pyridine, pyrimidine, thiophen and pyrrole.

11. The process as claimed in claim 1, wherein A is selected from the group consisting of a methyl, a propyl sulfonate, an ethyl sulfonate and a methylphosphate.

12. The process as claimed in claim 1, wherein the linear or branched saturated $C_1$-$C_{20}$ carbon chain interrupted by 1 to 10 oxygen atoms of each of L and L" is a polyethylene oxide) or a poly(propylene oxide), the unit whereof repeats between one and six times.

\* \* \* \* \*